(12) United States Patent
Xu et al.

(10) Patent No.: US 6,858,439 B1
(45) Date of Patent: Feb. 22, 2005

(54) COMPOSITIONS AND METHODS FOR SEPARATION OF MOIETIES ON CHIPS

(75) Inventors: Junquan Xu, Beijing (CN); Xiaobo Wang, San Diego, CA (US); Jing Cheng, Beijing (CN); Weiping Yang, San Diego, CA (US); Lei Wu, San Diego, CA (US)

(73) Assignee: Aviva Biosciences, San Diego, CA (US)

(*) Notice: Subject to any disclaimer, the term of this patent is extended or adjusted under 35 U.S.C. 154(b) by 408 days.

(21) Appl. No.: 09/686,737

(22) Filed: Oct. 10, 2000

Related U.S. Application Data

(63) Continuation-in-part of application No. 09/636,104, filed on Aug. 10, 2000, and a continuation-in-part of application No. 09/399,299, filed on Sep. 17, 1999, now Pat. No. 6,355,491.

(30) Foreign Application Priority Data

Mar. 15, 1999 (CN) ........................................ 99104113 A
Aug. 8, 2000 (CN) ........................................ 00122631 A

(51) Int. Cl.[7] ............................................ G01N 33/543
(52) U.S. Cl. ...................... 436/518; 436/519; 436/520; 436/522; 436/524; 436/538; 436/541; 436/809; 436/174; 436/177; 436/178; 436/179; 436/180; 435/7.2; 435/7.35; 435/7.33; 435/7.34; 435/7.36; 435/4; 435/5; 422/50; 204/463; 204/450; 204/600; 204/409; 204/403
(58) Field of Search ................................ 436/518, 519, 436/520, 522, 524, 538, 541, 809, 810, 174, 177, 178, 179, 180; 435/4, 5, 7.2, 7.35, 7.33, 7.34, 7.36, 285; 422/50; 204/463, 450, 600, 409, 403

(56) References Cited

U.S. PATENT DOCUMENTS 4,160,645 A 7/1979 Ullman
4,275,149 A 6/1981 Litman et al.
4,318,980 A 3/1982 Boguslaski et al.
4,326,934 A 4/1982 Pohl
4,390,403 A 6/1983 Batchelder (List continued on next page.)

FOREIGN PATENT DOCUMENTS

WO  WO 94/16101 A3  7/1994
WO  WO 94/16101 A2  7/1994

OTHER PUBLICATIONS

1992 Products for Molecular Biology, Molecular Sigma Biology, p. 83–86.*

(List continued on next page.)

*Primary Examiner*—Christopher L. Chin
*Assistant Examiner*—Pensee T. Do
(74) *Attorney, Agent, or Firm*—David R. Preston & Associates A. P.C.; Elizabeth Orr; David Preston

(57) ABSTRACT

The present invention recognizes that separation of components of a sample facilitate, and are often necessary for, sample analysis. Dielectrophoretic separation provides an efficient, reliable, nondisruptive, and automatable method for the separation of moieties in a sample based on their dielectric properties. The present invention provides compositions and methods for enhancing the dielectrophoretic separation of one or more moieties in a sample. A first aspect of the present invention is a solution that when mixed with a sample, modifies at least one dielectric property of one or more components of the sample and has a conductivity such that one or more moieties of the sample can be separated using dielectrophoresis. Such solutions can be used in the analysis of samples on chips, and can be used in methods that use binding partners, including microparticles that can be translocated by dielectrophoretic forces, traveling-wave dielectrophoretic forces or magnetic forces.

27 Claims, 5 Drawing Sheets

U.S. PATENT DOCUMENTS

| | | | |
|---|---|---|---|
| 4,783,401 A | * | 11/1988 | Horan et al. |
| 4,894,443 A | | 1/1990 | Greenfield et al. |
| 5,344,535 A | | 9/1994 | Betts et al. |
| 5,454,472 A | | 10/1995 | Benecke et al. |
| 5,536,382 A | * | 7/1996 | Sunzeri |
| 5,569,367 A | | 10/1996 | Betts et al. |
| 5,578,460 A | * | 11/1996 | Ebersole et al. |
| 5,581,349 A | * | 12/1996 | Halaka |
| 5,612,474 A | | 3/1997 | Patel |
| 5,653,859 A | | 8/1997 | Parton et al. |
| 5,795,457 A | | 8/1998 | Pethig et al. |
| 5,814,200 A | | 9/1998 | Pethig et al. |
| 5,858,192 A | | 1/1999 | Becker et al. |
| 5,883,760 A | | 3/1999 | Yamada et al. |
| 5,888,370 A | | 3/1999 | Becker et al. |
| 5,993,630 A | | 11/1999 | Becker et al. |
| 5,993,631 A | | 11/1999 | Parton et al. |
| 5,993,632 A | * | 11/1999 | Becker et al. |
| 6,071,394 A | * | 6/2000 | Cheng et al. |
| 6,200,500 B1 | * | 3/2001 | Ryan |
| 6,280,590 B1 | * | 8/2001 | Cheng et al. |
| 6,287,832 B1 | * | 9/2001 | Becker et al. |
| 6,432,630 B1 | * | 8/2002 | Blankenstein |

OTHER PUBLICATIONS

Ahn et al., IEEE Trans. Magnetics, 30:73–79 (1994).
Ahn et al., J. Micromechanical Systems, 5:151–157 (1996).
Batra et al., Mol. Immunology, 30:379–386 (1993).
Becker et al., J. Phys. D: Appl. Phys., 27:2659–2662 (1994).
Becker et al., Proc. Natl. Acad. Aci. USA 92:860–864 (1995).
Burt et al., J. Phys. E: Sci. Instrum., 22:952–957 (1989).
Cheng et al., Nat. Biotech., 16:541–546 (1998).
Cumber et al., Bioconjugate Chem., 3:397–401 (1992).
De Gasperis et al., Biomedical Microdevices, 2:41–49 (1999).
Edman et al., Nucleic Acids Res., 25:4907–4914 (1997).
Fiedler et al., Anal. Chem., 70:1909–1915 (1998).
Fiedler et al., Microsystem Technologies, 2:1–7 (1995).
Fuhr et al., Biochim. Biophys. Acta, 1108:215–223 (1992).
Fuhr et al., Sensors and Actuators A., 41:230–239 (1994).
Fuhr et al., Cellular Engineering, Autumn:47–57 (1995).
Fuhr et al., Sensors and Materials, 7:131–146 (1995).
Gascoyme et al., IEEE Transactions on Ind. Appl., 33:670–678 (1997).
Green and Morgan, J. Phys. D: Appl. Phys., 30:L41–L44 (1997).
Hagedorn et al., Electrophoresis, 13:49–54 (1992).
Hagedorn et al., J. Electrostatics, 33:159–185 (1994).
Hawkes et al., Microbios., 73:81–86 (1993).
Huang and Pethig, Meas. Sci. Technol., 2:1142–1146 (1991).
Huang et al., Phys. Med. Biol., 37:1499–1517 (1992).
Huang et al., J. Phys. D: Appl. Phys., 26:1528–1535 (1993).
Huang et al., Phys. Med. Biol., 40:1789–1806 (1995).
Huang et al., Biochim. Biophys. Acta, 1282:76–84 (1996).
Huang et al., Biophys. J., 73:1118–1129 (1997).
Huang et al., Biochim. Biophys. Acta, 1417:51–62 (1999).
Hughes et al., Biochim. Biophys. Acta, 1425:119–126 (1998).
Huston et al., Proc. Natl. Acad. Sci. USA, 85:5879–5883 (1988).
Ladurner et al., J. Mol. Biol., 273:330–337 (1997).
Liakopoulos et al., Transducers '97, pp. 485–488 (1997).
Markx et al., Microbiology, 140:585–591 (1994).
Morgan et al., Biophys. J., 77:516–525 (1999).
Muller et al., Biosensors and Bioelectronics, 14:247–256 (1999).
Newton et al., Biochemistry, 35:545–553 (1996).
Price et al., Bioichim. Biophys Acta, 954:221–230 (1988).
Schnelle et al., Biochim. Biophys. Acta, 1157:127–140 (1993).
Stephens et al., Bone Marrow Transplantation, 18:777–782 (1996).
Wang et al., J. Phys. D: Appl. Phys., 26:1278–1285 (1993).
Wang et al., Biochim. Biophys. Acta., 1243:185–194 (1995).
Wang et al., IEEE Transactions on Industry Appl., 33:660–669 (1997).
Wang et al., Biophys. J., 72:1887–1899 (1997).
Wang et al., Biophys. J., 74:2689–2701 (1998).
Washizu et al., IEEE Transactions on Industry Appl., 26:352–358 (1990).
Washizu et al., IEEE Transactions on Industry Appl., 30:835–843 (1994).
Whitlow et al., Protein Engineering, 6:989–995 (1993).
Yang et al., Anal. Chem., 71:911–918 (1999).

* cited by examiner

COMPOSITIONS AND METHODS FOR SEPARATION OF MOIETIES ON CHIPS

This application of priority to continuation in-part pending U.S. patent application Ser. No. 09/636,104 filed Aug. 10, 2000, entitled "Methods for Manipulating Moieties in Microfluidic Systems", and to People's Republic of China Patent Application 0012263.1.2, filed Aug. 8, 2000, and to PCT Patent Application Number PCT/US00/25381 entitled "Method for Manipulating Moieties in Microfluidic Systems" filed Sep. 15, 2000, and naming Xiaobo Wang, Lei Wu, Jing Cheng, Weiping Yang, and Junquan Yu as inventors, all herein incorporated by reference in their entireties.

This application also continuation-in-part of priority to U.S. patent application Ser. No. 09/399,299,filed Sep. 17, 1999, now U.S. Pat. No. 6,355,491 entitled, "Individually Addressable Micro-Electromagnetic Unit Array Chips"; and to People's Republic of China Application Number 99104113.5, entitled "Individually Addressable Micro-Electromagnetic Unit Array Chips, Electromagnetic Biochips, and Their Applications", filed Mar. 15, 1999; and PCT Application No. PCT/US99/21417, filed Sep. 17, 1999, entitled "Individually Addressable Micro-Electromagnetic Unit Array Chips"; all of which are herein incorporated by reference in their entireties.

The following applications are incorporated herein by reference in their entirety:

U.S. patent application Ser. No. 09/648,081 entitled "Methods and Compositions for Identifying Nucleic Acid Molecules Using Nucleolytic Activities and Hybridization" naming as inventors Guoqing Wang, Lei Wu, Xiaobo Wang, Jing Cheng, and WeiPing Yang, and filed on Aug. 25, 2000.

U.S. application Ser. No. 09/678,263, entitled "Apparatus for Switching and Manipulating Particles and Methods of Use Thereof" filed on Oct. 3, 2000 and naming as inventors Xiaobo Wang, Weiping Yang, Junquan Xu, Jing Cheng, and Lei Wu;

U.S. application Ser. No. 09/079,024, entitled "Apparatuses Containing Multiple Active Force Generating Elements and Uses Thereof" filed Oct. 4, 2000, and naming as inventors Xiaobo Wang, Jing Cheng, Lei Wu, Junquan Xu, and Weiping Yang.

U.S. application Ser. No. 09/685,410, filed Oct. 10, 2000, entitled "Individually Addressable Micro-Electromagnetic Unit Array Chips in Horizontal Configurations" and naming Lei Wu, Xiaobo Wang, Jing Chen, Weiping Yang, YuXiang Zhou, LiTian Liu, and JunXuan Xu as inventors.

U.S. application Ser. No. 08/239,299, filed Oct. 10, 2000, entitled "An Integrated Biochip System for Sample Preparation and Analysis" and naming Jing Cheng, Xiaobo Wang, Lei Wu, Weiping Yang, and Xiao Yu as inventors.

TECHNICAL FIELD

The present invention relates generally to the field of bioseparation, in particular to the dielectrophoretic and magnetic separation of moieties on chips.

BACKGROUND

Sample preparation is a necessary step for the many genetic, biochemical, and biological analyses of biological and environmental samples. Sample preparation frequently requires the separation of sample components of interest from the remaining components of the sample. Such separations are often labor intensive and difficult to automate. In many cases, the preparation of a sample requires substantial purification of one or more components of the sample that can subsequently be analyzed. Dielectrophoresis, also sometimes called "conventional dielectrophoresis" to distinguish it from travelling wave dielectrophoresis, is the translocation of neutral or charged particles in response to an electric field of non-uniform magnitude. Dielectrophoresis and travelling wave dielectrophoresis provide efficient, reliable, nondisruptive, and automatable methods for the separation of particles in a sample based on their dielectric properties.

Dielectrophoresis and traveling-wave-dielectrophoresis have been used, for example, to separate breast cancer cells from blood (Becker et al., Proc. Natl. Acad. Sci. USA 92: 860–864 (1995)); to separate bacteria from blood cells (Hawkes et al., Microbios. 73: 81–86 (1993) and Cheng et al., Nat. Biotech. 16: 546–547 (1998)); to enrich CD34+ stem cells from blood (Stephens et al., Bone Marrow Transplantation 18: 777–782 (1996)); and to collect viral particles, submicron beads, and biomolecules (Washizu, et al, IEEE Trans. Ind. App. 30: 835–843 (1994), Green and Morgan, J. Phys. D: Appl. Phys. 30: L41–L44 (1997), Hughes et al., Biochim. Biophys. Acta 1425:119–126 (1998), and Morgan et al., Biophys. J. 77: 516–525 (1999). The separation of particles, including cells, using dielectrophoresis is also described in U.S. Pat. No. 4,390,403 issued Jun. 28,1983; U.S. Pat. No. 4,326,934 issued Apr. 27, 1982 to Pohl; U.S. Pat. No. 5,344,535 issued Sep. 6, 1994 to Betts and Hawkes; U. S. Pat. No. 5,454,472 issued Oct. 3, 1995 to Benecke et al.; U.S. Pat. No. 5,569,367 issued Oct. 29, 1996 to Betts et al.; U.S. Pat. No. 5,653,859 issued Aug. 5, 1997; U.S. Pat. No. 5,795,457 issued Aug. 18, 1998 to Pethig, et al.; U.S. Pat. No. 5,814,200 issued Sep. 29, 1998 to Pethig et al.; U.S. Pat. No. 5,858,192 issued Jan. 12, 1999 to Becker et al.; U.S. Pat. No. 5,888,370 issued Mar. 30, 1999; U.S. Pat. No. 5,993,630 issued Nov. 30, 1999 to Becker et al.; U.S. Pat. No. 5,993,631 issued Nov. 30, 1999 to Parton et al.; and U.S. Pat. No. 5,993,632 issued Nov. 30, 1999 to Becker et al.

Dielectrophoresis refers to the translational movement of polarized particles in an alternating current (AC) electrical field of non-uniform magnitude. When a particle is placed in an electrical field, if the dielectric properties of the particle and its surrounding medium are different, dielectric polarization will occur to the particle. Thus, electrical charges are induced at the particle/medium interface. If the applied field is non-uniform, then the interaction between the non-uniform field and the induced polarization charges will produce net force acting on the particle to cause particle motion towards the region of strong or weak field intensity. The net force acting on the particle is called the dielectrophoretic force and the particle motion is dielectrophoresis. The dielectrophoretic force acting on a particle depends on the dielectric properties of the particle, the dielectric properties of the particle surrounding medium, the frequency and magnitude of the applied electrical field, and the field magnitude distribution. In the literature, dielectrophoresis is sometimes called conventional dielectrophoresis (e.g. in Wang et al. Biochim. Biophys. Acta 1243: 185–194 (1995)). For simplicity, in the present application, we use the term "dielectrophoresis" to refer the motion of polarized particles in a field of non-uniform magnitude. The corresponding forces that act on the polarized particles are "dielectrophoretic forces".

Separation techniques that use dielectrophoresis are dielectrophoretic retention (or dielectrophoretic affinity), dielectrophoretic migration, and dielectrophoretic/gravitational-field flow fractionation (DEP/G-FFF). In dielectrophoretic retention, one or more particles of a sample that experiences a positive dielectrophoretic force is attracted to and retained in one or more areas of a chip or chamber that are regions of electric field maxima, typically at electrode edges. In separation procedures where dielectrophoretic retention is used, components of a sample that experience negative dielectrophoretic forces or weakly positive dielectrophoretic forces generally are flushed out of the chamber by fluid flow. In dielectrophoretic migration, particles are separated based on the different dielectrophoretic forces they experience. For example, one or more particles can experience negative dielectrophoretic forces and migrate to one area of a chamber and one or more different particles can experience positive dielectrophoretic forces and migrate to a different area of a chamber. In dielectrophoretic/gravitational-field flow fractionation (DEP/G-FFF), particles can be levitated by negative dielectrophoretic forces. Different particles are levitated to different extent in the chamber and are subjected to a fluid flow profile. Different particles levitated to different heights in the chamber are carried with the fluid flow at different speeds and thereby separated.

Travelling wave dielectrophoreis (TW-DEP), also called "travelling wave field migration" or TWFM, is related to dielectrophoresis (or sometimes called conventional dielectrophoresis), described above. In travelling-wave dielectrophoresis, the electric field has a non-uniform phase distribution. The travelling-wave electric field interacts with the field-induced polarization of particles and generates forces acting on the particles. Particles are caused to move either with or against the traveling direction of the traveling field. Travelling-wave dielectrophoretic forces depend on the dielectric properties of the particles and their suspending medium, on the frequency and magnitude of the traveling field, and on the phase value distribution of the traveling field. In "2-dimensional dielectrophoresis" (2-D DEP) particles are separated by exploiting both dielectrophoretic forces and travelling wave dielectrophoresis forces acting on particles (De Gasperis et al., Biomedical Microdevices 2: 41–49 (1999)). Furthermore, in 2-D DEP, particles are subjected to a fluid flow profile.

The theory for dieletrophoresis and traveling-wave dielectrophoresis and the use of dielectrophoresis for manipulation and processing of microparticles may be found in the following references: Wang et al. Biochim. Biophys. Acta 1243: 185–194.(1995); Wang et al. IEEE Transaction on Industry Applications 33: 660–669 (1997); Huang et al. J. Phys. D: Appl. Phys. 26: 1528–1535 (1993); Fuhr et al., Sensors and Materials 7: 131–146; Wang et al. Biophys. J. 72: 1887–1899 (1997); and Becker et al. Proc. Natl. Acad. Sci. 92: 860–864 (1995).

The manipulation of microparticles, including synthetic particles, crystals, colloids, molecules, compounds, molecular complexes, cells, and organelles, with dielectrophoresis and travelling-wave dielectrophoresis include concentration, aggregation, trapping, repulsion, linear or other directed motion, levitation, and separation of particles. Particles may be focused, enriched, and trapped in specific regions of the reaction chamber. Particles may be separated into different subpopulations over a microscopic scale, or may be transported over certain distances. The electrical field distribution necessary for specific particle manipulation depends on the dimension and geometry of electrode structures and may be designed using dielectrophoresis theory and electrical field simulation methods.

In many cases, however, it is difficult to separate components of a sample using dielectrophoretic forces and/or travelling wave dielectrophoretic forces because the dielectric properties of the moieties (e.g, cells or molecules) to be separated are similar. In other instances, it is difficult to separate moieties in a sample because of the small sizes of the moieties. Because the dielectrophoretic force on a moiety is proportional to the size of the moiety to be translocated, small moieties such as molecules (for example, nucleic acid molecules and proteins) require very large electric fields, and thus, very large applied voltages, for their manipulation. Such high voltages can damage biological materials, such as cells. High voltages can also cause heating of the separation medium, with potentially deleterious effects to both biological and nonbiological materials. There is a need for methods that can provide for the efficient separation of moieties regardless of their size or intrinsic dielectric properties.

Blood samples provide a special challenge for sample preparation and analysis. Blood samples are easily sampled from subjects, and can provide a wealth of metabolic, diagnostic, prognostic, and genetic information. However, the abundance of non-nucleated red blood cells, and their major component hemoglobin, can be an impediment to genetic, metabolic, and diagnostic tests. Removal of red blood cells can be achieved through centrifugation or filtering, which require extra steps and efforts that are not easily automatable. In other procedures, red blood cells are removed from blood samples by first lysing red blood cells and then collecting other cells through centrifugation. Lysis buffers used in these procedures tend to have undesirable effects on white blood cells. Thus there is typically a time window in which separation should be completed to avoid damage to the white blood cells, which can be inconvenient for the technician analyzing the sample. In addition, the use of centrifugation requires additional steps and efforts that are not easily automatable.

SUMMARY

Figure 1:
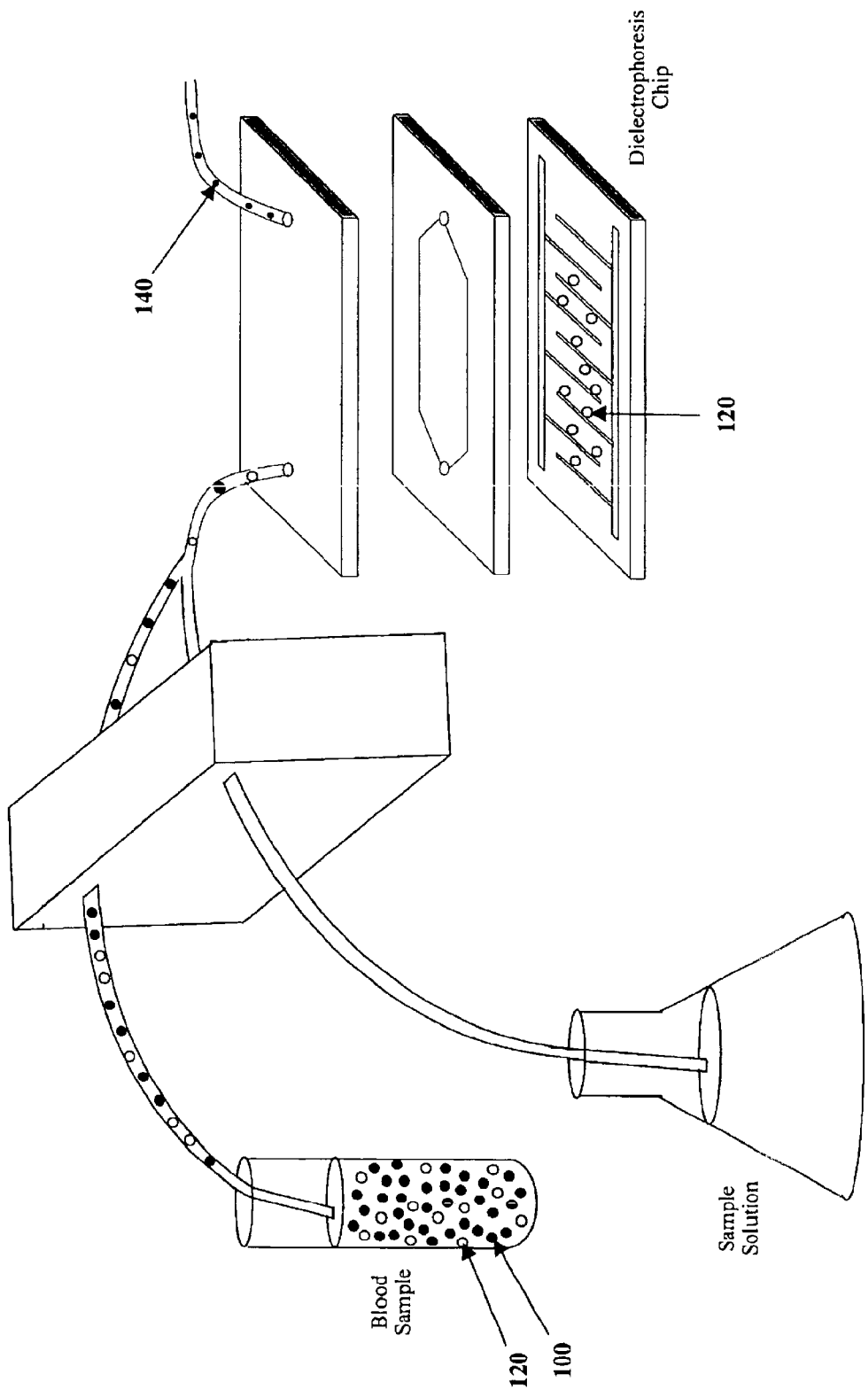
FIG. 1 depicts one aspect of a method of the present invention, where a sample solution of the present invention is added to a blood sample comprising red blood cells (100) and white blood cells (120) via a branched conduit. White blood cells (120) of the sample are separated on a chip by dielectrophoretic retention on an interdigitated parallel electrode array, and fragments of red blood cells (140) are removed from the chamber by fluid flow. The chamber is shown opened to reveal the electrode array. In operation, the chamber is closed.

The present invention recognizes that separation of components of a sample facilitate, and are often necessary for, sample analysis. Dielectrophoretic separation provides an efficient, reliable, nondisruptive, and automatable method for the separation of moieties in a sample based on their dielectric properties. The present invention provides compositions and methods for enhancing the dielectrophoretic separation of one or more moieties in a sample.

A first aspect of the present invention is a solution that when mixed with a sample, modifies at least one dielectric property of one or more components of the sample and has a conductivity such that one or more moieties of the sample can be separated using dielectrophoresis. Such solutions can be used in the analysis of samples on chips, and can be used in methods that use binding partners, including microparticles that can be translocated by dielectrophoretic forces, traveling-wave dielectrophoretic forces or magnetic forces.

A second aspect of the present invention is a method of dielectrophoretically separating one or more moieties in a sample using a solution of the present invention that selectively modifies at least one dielectric property of one or more components of the sample and has a conductivity such that one or more moieties of the sample can be separated using dielectrophoretic or traveling-wave dielectrophoretic forces. The method can optionally include microparticles that can be coupled to a moiety and can be translocated by dielectrophoresis.

A third aspect of the invention is a method of separating one or more moieties in a sample using magnetic microparticles that can be bound to moieties to be separated, a solution that selectively modifies red blood cells, and electromagnetic forces. The electromagnetic forces can be produced by electromagnetic elements or structures that are integral to a chip used for separation.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of parts during use of a device. Where a term is provided in the singular, the inventors also contemplate the plural of that term. The nomenclature used herein and the laboratory procedures described below are those well known and commonly employed in the art. Where there are discrepancies in terms and definitions used in references that are incorporated by reference, the terms used in this application shall have the definitions given herein. As employed throughout the disclosure, the following terms, unless otherwise indicated, shall be understood to have the following meanings:

A solution having "low osmolarity" is a solution that is hypotonic with respect to blood cells, and should be less than about 300 mOsm.

A "solution that selectively lyses red blood cells" is a solution that, when mixed with a sample that contains red blood cells, can lyse, permeabilize, or otherwise alter the structural integrity of red blood cells in a sample, such that when suspended in the sample-solution mixture they are no longer responsive to dielectrophoretic forces used in the invention to separate other cells or moieties in the sample-sample solution mixture.

A solution with "low conductivity" is a solution in which a moiety of interest can exhibit positive dielectrophoresis under dielectrophoretic separation conditions. Preferably, a low conductivity solution has a conductivity between about 1 microSiemen/cm and about 1 Siemen/m, more preferably between about 5 microSiemens/cm and about 0.5 Siemen/m, and most preferably between about 10 microSiemens/cm and about 0.1 Siemen/m.

"Dielectrophoresis" is the movement of polarized particles in electrical fields of nonuniform strength. There are generally two types of dielectrophoresis, positive dielectorphoresis and negative dielectrophoresis. In positive dielectrophoresis, particles are moved by dielectrophoretic forces toward the strong field regions. In negative dielectrophoresis, particles are moved by dielectrophoretic forces toward weak field regions. Whether moieties exhibit positive or negative dielectrophoresis depends on whether particles are more or less polarizable than the surrounding medium.

A "dielectrophoretic force" is the force that acts on a polarizable particle in an AC electrical field of non-uniform strength. The dielectrophoretic force $\vec{F}_{DEP}$ acting on a particle of radius r subjected to a non-uniform electrical field can be given by:

$$\vec{F}_{DEP} = 2\pi \epsilon_m r^3 \chi_{DEP} \nabla E_{rms}^2$$

where $E_{rms}$ is the RMS value of the field strength, the symbol $\nabla$ is the symbol for gradient-operation, $\epsilon_m$ is the dielectric permittivity of the medium, and $\chi_{DEP}$ is the particle polarization factor, given by:

$$\chi_{DEP} = \text{Re}\left(\frac{\epsilon_p^* - \epsilon_m^*}{\epsilon_p^* + 2\epsilon_m^*}\right),$$

"Re" refers to the real part of the "complex number". The symbol $\epsilon^*_x = \epsilon_x - j\sigma_x/2\pi f$ is the complex permittivity (of the particle x=p, and the medium x=m) and $j=\sqrt{-1}$. The parameters $\epsilon_p$ and $\sigma_p$ are the effective permittivity and conductivity of the particle, respectively. These parameters may be frequency dependent. For example, a typical biological cell will have frequency dependent, effective conductivity and permittivity, at least, because of cytoplasm membrane polarization. Particles such as biological cells having different dielectric property (as defined by permittivity and conductivity) will experience different dielectrophoretic forces.

The above equation for the dielectrophoretic force can also be written as $$\vec{F}_{DEP} = 2\pi \epsilon_m r^3 \chi_{DEP} V^2 \nabla p(x,y,z)$$

where p(x,y,z) is the square-field distribution for an unit-voltage excitation (Voltage V=1 V) on the electrodes, V is the applied voltage.

"Travelling-wave dielectrophotetic (TW-DEP) force" refers to the force that is generated on particles or molecules due to a traveling-wave electric field. An ideal traveling-wave field is characterized by the distribution of the phase values of AC electric field components, being a linear function of the position of the particle. In this case the travelling wave dielectrophoretic force $\vec{F}_{TW-DEP}$ on a particle of radius r subjected to a travelling wave electrical field $E = E \cos(2\pi(ft-z/\lambda_0)) \vec{a}_x$ (i. e., a x-direction field is traveling along the z-direction) is given by $$\vec{F}_{TW-DEP} = -\frac{4\pi^2 \varepsilon_m}{\lambda_0} r^3 \zeta_{TW-DEP} E^2 \cdot \vec{a}_z$$

where E is the magnitude of the field strength, $\varepsilon_m$ is the dielectric permittivity of the medium. $\zeta_{TW-DEP}$ is the particle polarization factor, given by $$\zeta_{TW-DEP} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $\varepsilon^*_x = \varepsilon_x - j\sigma_x/2\pi f$ is the complex permittivity (of the particle x=p, and the medium x=m). The parameters $\varepsilon_p$ and $\sigma_p$ are the effective permittivity and conductivity of the particle, respectively. These parameters may be frequency dependent.

A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quardrature signals (0, 90, 180 and 270 degrees) to energize four linear, parallel electrodes patterned on the chip surfaces. Such four electrodes may be used to form a basic, repeating unit. Depending on the applications, there may be more than two such units that are located next to each other. This will produce a traveling-electric field in the spaces above or near the electrodes. As long as electrode elements are arranged following certain spatially sequential orders, applying phase-sequenced signals will result in establishing traveling electrical fields in the region close to the electrodes.

"Electric field pattern" refers to the field distribution in space or in a region of interest. An electric field pattern is determined by many parameters, including the the frequency of the field, the magnitude of the field, the magnitude distribution of the field, the distribution of the phase values of the field components, the geometry of the electrode structures that produce the electric field, and the frequency and/or magnitude modulation of the field.

"Dielectric properties" of a moiety are properties that determine, at least in part, the response of a moiety to an electric field. The dielectric properties of a moiety include the effective electric conductivity of a moiety and the effective electric permittivity of a moiety. For a particle of homogeneous composition, for example, a polystyrene bead, the effective conductivity and effective permittivity are independent of the frequency of the electric field at least for a wide frequency range (e.g. between 1 Hz to 100 MHz). Particles that have a homoegeneous bulk composition may have net surface charges. When such charged particles are suspended in a medium, electrical double layers may form at the particle/medium interfaces. Externally applied electric field may interact with the electrical double layers, causing changes in the effective conductivity and effective permittivity of the particles. The interactions between the applied field and the electrical double layers are generally frequency dependent. Thus, the effective conductivity and effective permittivity of such particles may be frequency dependent. For moieties of nonhomogeneous composition, for a example, a cell, the effective conductivity and effective permittivity are values that take into account the effective conductivities and effective permittivities of both the membrane and internal portion of the cell, and can vary with the frequency of the electric field. In addition, the dielectrophoretic force experience by a moiety in an electric field is dependent on its size; therefore, the overall size of moiety is herein considered to be a dielectric property of a moiety. Properties of a moiety that contribute to its dielectric properties include the net charge on a moiety; the composition of a moiety (including the distribution of chemical groups or moieties on, within, or throughout a moiety); size of a moiety; surface configuration of a moiety; surface charge of a moiety; and the conformation of a moiety.

"Magnetic forces" refer to the forces acting on a particle due to the application of a magnetic field. In general, particles have to be magnetic or paramagnetic when sufficient magnetic forces are needed to manipulate particles. For a typical magnetic particle made of super-paramagnetic material, when the particle is subjected to a magnetic field $\vec{B}$, a magnetic dipole $\vec{\mu}$ is induced in the particle $$\vec{\mu} = V_p(\chi_p - \chi_m)\frac{\vec{B}}{\mu_m},$$
$$= V_p(\chi_p - \chi_m)\vec{H}_m$$

where $V_p$ is the particle volume, $\chi_p$ and $\chi_m$ are the volume susceptibility of the particle and its surrounding medium, $\mu_m$ is the magnetic permeability of medium, $\vec{H}_m$ is the magnetic field strength. The magnetic force $\vec{F}_{magnetic}$ acting on the particle is determined by the magnetic dipole moment and the magnetic field gradient:

$$\vec{F}_{magnetic} = -0.5 V_p(\chi_p - \chi_m)\vec{H}_m \cdot \nabla \vec{B}_m,$$

where the symbols "·" and "∇" refer to dot-product and gradient operations, respectively. Whether there is magnetic force acting on a particle depends on the difference in the volume susceptibility between the particle and its surrounding medium. Typically, particles are suspended in a liquid, non-magnetic medium (the volume susceptibility is close to zero) thus it is necessary to utilize magnetic particles (its volume susceptibility is much larger than zero). The particle velocity $v_{particle}$ under the balance between magnetic force and viscous drag is given by:

$$v_{particle} = \frac{\vec{F}_{magnetic}}{6\pi r \eta_m}$$

where r is the particle radius and $\eta_m$ is the viscosity of the surrounding medium.

A "component" of a sample or "sample component" is any constituent of a sample, and can be an ion, molecule, compound, molecular complex, organelle, virus, cell, aggregate, or particle of any type, including colloids, aggregates, particulates, crystals, minerals, etc. A component of a sample can be soluble or insoluble in the sample media or a provided sample buffer or sample solution. A component of a sample can be in gaseous, liquid, or solid form. A component of a sample may be a moiety or may not be a moiety.

A "moiety" or "moiety of interest" is any entity, whose manipulation by dielectrophoretic or traveling-wave dielectrophoretic or electromagnetic forces is desireable. A moiety can be a solid, including a suspended solid, or can be in soluble form. A moiety can be a molecule. Molecules that can be manipulated include, but are not limited to, inorganic molecules, including ions and inorganic compounds, or can be organic molecules, including amino acids, peptides, proteins, glycoproteins, lipoproteins, glycolipoproteins, lipids, fats, sterols, sugars, carbohydrates, nucleic acid molecules, small organic molecules, or complex organic molecules. A moiety can also be a molecular complex, can be an organelle, can be one or more cells, including prokaryotic and eukaryotic cells, or can be one or more etiological agents, including viruses, parasites, or prions, or portions thereof. A moiety can also be a crystal, mineral, colloid, fragment, or the like, and can comprise one or more inorganic materials such as polymeric materials, metals, minerals, glass, ceramics, and the like. Moieties can also be aggregates of molecules, complexes, cells, organelles, viruses, etiological agents, crystals, colloids, or fragments. Cells can be any cells, including prokaryotic and eukaryotic cells. Eukaryotic cells can be of any type. Of particular interest are cells such as, but not limited to, white blood cells, malignant cells, stem cells, progenitor cells, fetal cells, and cells infected with an etiological agent, and bacterial cells.

As used herein, "intracellular moiety" refers to any moiety that resides or is otherwise located within a cell, i.e., located in the cytoplasm or matrix of cellular organelle, attached to any intracellular membrane, resides or is otherwise located within periplasm, if there is one, or resides or is otherwise located on cell surface, i.e., attached on the outer surface of cytoplasm membrane or cell wall, if there is one.

As used herein, "manipulation" refers to moving or processing of the moieties, which results in one-, two- or three-dimensional movement of the moiety, in a chip format, whether within a single chip or between or among multiple chips. Non-limiting examples of the manipulations include transportation, focusing, enrichment, concentration, aggregation, trapping, repulsion, levitation, separation, isolation or linear or other directed motion of the moieties. For effective manipulation, the binding partner and the physical force used in the method must be compatible. For example, binding partners with magnetic properties must be used with magnetic force. Similarly, binding partners with certain dielectric properties, e.g., plastic particles, polystyrene microbeads, must be used with dielectrophoretic force.

As used herein, "the moiety to be manipulated is substantially coupled onto surface of the binding partner" means that a percentage of the moiety to be manipulated is coupled onto surface of the binding partner and can be manipulated by a suitable physical force via manipulation of the binding partner. Ordinarily, at least 0.1% of the moiety to be manipulated is coupled onto surface of the binding partner. Preferably, at least 1%, 5%, 10%, 20%, 30%, 40%, 50%, 60%, 70%, 80% or 90% of the moiety to be manipulated is coupled onto surface of the binding partner.

As used herein, "the moiety to be manipulated is completely coupled onto surface of the binding partner" means that at least 90% of the moiety to be manipulated is coupled onto surface of the binding partner. Preferably, at least 91%, 92%, 93%, 94%, 95%, 96%, 97%, 98%, 99% or 100% of the moiety to be manipulated is coupled onto surface of the binding partner. A "solution that selectively modifies red blood cells" is a solution that alters non-nucleated red blood cells such that they do not interfere with the dielectrophoretic separation of other cells or components of a blood sample, without substantially altering the integrity of white blood cells, or interfering with the ability of white blood cells to be dielectrically separated from other components of a blood sample.

A "sample" is any fluid from which components are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample.

A "blood sample" as used herein can refer to a processed or unprocessed blood sample, i.e., it can be a centrifuged, filtered, extracted, or otherwise treated blood sample, including a blood sample to which one or more reagents such as, but not limited to, anticoagulants or stabilizers have been added. An example of blood sample is a buffy coat that is obtained by processing human blood for enriching white blood cells. A blood sample can be of any volume, and can be from any subject such as an animal or human. A preferred subject is a human.

A "white blood cell" is a leukocyte, or a cell of the hematopoietic lineage that is not a reticulocyte or platelet and that can be found in the blood of an animal. Leukocytes can include lymphocytes, such as B lymphocytes or T lymphocytes. Leukocytes can also include phagocytic cells, such as monocytes, macrophages, and granulocytes, including basophils, eosinophils and neutrophils. Leukocytes can also comprise mast cells.

A "red blood cell" is an erythrocyte.

"Neoplastic cells" refers to abnormal cells that grow by cellular proliferation more rapidly than normal and can continue to grow after the stimuli that induced the new growth has been withdrawn. Neoplastic cells tend to show partial or complete lack of structural organization and functional coordination with the normal tissue, and may be benign or malignant.

A "malignant cell" is a cell having the property of locally invasive and destructive growth and metastasis.

A "stem cell" is an undifferentiated cell that can give rise, through one or more cell division cycles, to at least one differentiated cell type.

A "progenitor cell" is a committed but undifferentiated cell that can give rise, through one or more cell division cycles, to at least one differentiated cell type. Typically, a stem cell gives rise to a progenitor cell through one or more cell divisions in response to a particular stimulus or set of stimuli, and a progenitor gives rise to one or more differentiated cell types in response to a particular stimulus or set of stimuli.

An "etiological agent" refers to any etiological agent, such as a bacteria, virus, parasite or prion that can infect a subject. An etiological agent can cause symptoms or a disease state in the subject it infects. A human etiological agent is an etiological agent that can infect a human subject. Such human etiological agents may be specific for humans, such as a specific human etiological agent, or may infect a variety of species, such as a promiscuous human etiological agent.

"Subject" refers to any organism, such as an animal or a human. An animal can include any animal, such as a feral animal, a companion animal such as a dog or cat, an agricultural animal such as a pig or a cow, or a pleasure animal such as a horse.

A "chamber" is a structure that comprises a chip and that is capable of containing a fluid sample. The chamber may have various dimensions and its volume may vary between 0.001 microliter and 50 milliliter.

A "port" is an opening in the housing of a chamber through which a fluid sample can enter or exit the chamber. A port can be of any dimensions, but preferably is of a shape and size that allows a sample to be dispensed into a chamber by means of a pipette, syringe, or conduit, or other means of dispensing a sample.

A "conduit" is a means for fluid to be transported from a container to a chamber of the present invention. Preferably a conduit engages a port in the housing of a chamber. A conduit can comprise any material that permits the passage of a fluid through it. Preferably a conduit is tubing, such as, for example, rubber, teflon, or tygon tubing. A conduit can be of any dimensions, but preferably ranges from 10 microns to 5 millimeters in internal diameter.

A "chip" is a solid substrate on which one or more processes such as physical, chemical, biochemical, biological or biophysical processes can be carried out. Such processes can be assays, including biochemical, cellular, and chemical assays; separations, including separations mediated by electrical, magnetic, physical, and chemical (including biochemical) forces or interactions; chemical reactions, enzymatic reactions, and binding interactions, including captures. The micro structures or micro-scale structures such as, channels and wells, electrode elements, electromagnetic elements, may be incorporated into or fabricated on the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include channels or wells fabricated on the surfaces.

"Micro-scale structures" are structures integral to or attached on a chip, wafer, or chamber that have characteristic dimensions of scale for use in microfluidic applications ranging from about 0.1 micron to about 20 mm. Example of micro-scale structures that can be on chips of the present invention are wells, channels, scaffolds, electrodes, electromagnetic units, or microfabricated pumps or valves.

"Separation" is a process in which one or more components of a sample is spatially separated from one or more other components of a sample. A separation can be performed such that one or more moieties of interest is translocated to one or more areas of a separation apparatus and at least some of the remaining components are translocated away from the area or areas where the one or more moieties of interest are translocated to and/or retained in, or in which one or more moieties is retained in one or more areas and at least some or the remaining components are removed from the area or areas. Alternatively, one or more components of a sample can be translocated to and/or retained in one or more areas and one or more moieties can be removed from the area or areas. It is also possible to cause one or more moieties to be translocated to one or more areas and one or more moieties of interest or one or more components of a sample to be translocated to one or more other areas. Separations can be achieved through the use of physical, chemical, electrical, or magnetic forces. Examples of forces that can be used in separations are gravity, mass flow, dielectrophoretic forces, traveling-wave dielectrophoretic forces, and electromagnetic forces.

"Capture" is a type of separation in which one or more moieties is retained in one or more areas of a chip. In the methods of the present application, a capture can be performed when phsyical forces such as dielectrophoretic forces or electromagentic forces are acted to the moiety and direct the moiety to one or more areas of a chip.

An "assay" is a test performed on a sample or a component of a sample. An assay can test for the presence of a component, the amount or concentration of a component, the composition of a component, the activity of a component, etc. Assays that can be performed in conjunction with the compositions and methods of the present invention include, but not limited to, biochemical assays, binding assays, cellular assays, genetic assays, gene expression assays and protein expression assays.

A "reaction" is a chemical or biochemical process that changes the chemical or biochemical compostion of one or more molecules or compounds or that changes the interaction of one or more molecules with one or more other molecules or compounds. Reactions of the present invention may be catalyzed by enzymes, and include, but are not limited to, degradation reactions, synthetic reactions, modifying reactions, cleavage reactions or binding reactions.

A "binding assay" is an assay that tests for the presence or concentration of an entity by detecting binding of the entity to a specific binding member, or that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A "biochemical assay" is an assay that tests for the presence, concentration, or activity of one or more components of a sample.

A "cellular assay" is an assay that tests for a cellular process, such as, but not limited to, a metabolic activity, a catabolic activity, an ion channel activity, an intracellular signaling activity, a receptor-linked signaling activity, a transcriptional activity, a translational activity, or a secretory activity.

A "genetic assay" is an assay that tests for the presence or sequence of a genetic element, where a genetic element can be any segment of a DNA or RNA molecule, including, but not limited to, a gene, a repetitive element, a transposable element, a regulatory element, a relomere, a centromere, or DNA or RNA of unknown function. As nonlimiting examples, genetic assays can use nucleic acid hybridization techniques, can comprise nucleic acid sequencing reactions, or can use one or more polymerases, as, for example a genetic assay based on PCR. A genetic assay can use one or more detectable labels, such as, but not limited to, fluorochromes, radioisotopes, or signal generating systems.

A "gene expression assay (or " gene expression profiling assay") is an assay that tests for the presence or quantity of one or more gene expression products, i.e. messenger RNAs.

The one or more types of mRNAs can be assayed simultaneously on cells of the interest from a sample. For different applications, the number and/or the types of mRNA molecules to be assayed in the gene expression assays may be different.

A "protein expression assay" (or "protein expression profiling assay") is an assay that tests for the presence or quantity of one or more proteins. One or more types of protein can be assayed simultaneously on the cells of the interest from a sample. For different applications, the number and/or the types of protein molecules to be assayed in the protein expression assays may be different.

An "electrode" is a structure of highly electrically conductive material. A highly conductive material is a material with a conductivity greater than that of surrounding structures or materials. Suitable highly electrically conductive materials include metals, such as gold, chromium, platinum, aluminum, and the like, and can also include nonmetals, such as carbon and conductive polymers. An electrode can be any shape, such as rectangular, circular, castellated, etc. Electrodes can also comprise doped semi-conductors, where a semi-conducting material is mixed with small amounts of other other "impurity" materials. For example, phosphorous-doped silicon may be used as conductive materials for forming electrodes.

A "well" is a structure in a chip, with a lower surface surrounded on at least two sides by one or more walls that extend from the lower surface of the well or channel. The walls can extend upward from the lower surface of a well or channel at any angle or in any way. The walls can be of an irregular conformation, that is, they may extend upward in a sigmoidal or otherwise curved or multi-angled fashion. The lower surface of the well or channel can be at the same level as the upper surface of a chip or higher than the upper surface of a chip, or lower than the upper surface of a chip, such that the well is a depression in the surface of a chip. The sides or walls of a well or channel can comprise materials other than those that make up the lower surface of a chip. In this way the lower surface of a chip can comprise a thin material through which electrical (including dielectrophoretic, traveling-wave dielectrophoretic, electromagnetic) forces can be transmitted, and the walls of one or more wells and/or one or more channels can optionally comprise other insulating materials that can prevent the transmission of electrical forces. The walls of a well or a channel of a chip can comprise any suitable material, including silicon, glass, rubber, and/or one or more polymers, plastics, ceramics, or metals.

A "channel" is a structure in a chip with a lower surface and at least two walls that extend upward from the lower surface of the channel, and in which the length of two opposite walls is greater than the distance between the two opposite walls. A channel therefore allows for flow of a fluid along its internal length. A channel can be covered (a "tunnel") or open.

"Continuous flow" means that fluid is pumped or injected into a chamber of the present invention continuously during the separation process. This allows for components of a sample that are not selectively retained on a chip to be flushed out of the chamber during the separation process.

"Binding partner" refers to any substances that both bind to the moieties with desired affinity or specificity and are manipulatable with the desired physical force(s). Non-limiting examples of the binding partners include cells, cellular organelles, viruses, microparticles or an aggregate or complex thereof, or an aggregate or complex of molecules.

A "microparticle" is a structure of any shape and of any composition, that is manipulatable by desired physical force(s). The microparticles used in the methods could have a dimension from about 0.01 micron to about ten centimeters. Preferably, the microparticles used in the methods have a dimension from about 0.1 micron to about several hundred microns. Such particles or microparticles can be comprised of any suitable material, such as glass or ceramics, and/or one or more polymers, such as, for example, nylon, polytetrafluoroethylene (TEFLON™), polystyrene, polyacrylamide, sepharose, agarose, cellulose, cellulose derivatives, or dextran, and/or can comprise metals. Examples of microparticles include, but are not limited to, plastic particles, ceramic particles, carbon particles, polystyrene microbeads, glass beads, magnetic beads, hollow glass spheres, metal particles, particles of complex compositions, microfabricated free-standing microstructures, etc. The examples of microfabricated free-standing microstructures may include those described in "Design of asynchronous dielectric micromotors" by Hagedorn et al., in Journal of Electrostatics, Volume: 33, Pages 159–185 (1994). Particles of complex compositions refer to the particles that comprise or consists of multiple compositional elements, for example, a metallic sphere covered with a thin layer of non-conducting polymer film.

"A preparation of microparticles" is a composition that comprises microparticles of one or more types and can optionally include at least one other compound, molecule, structure, solution, reagent, particle, or chemical entity. For example, a preparation of microparticles can be a suspension of microparticles in a buffer, and can optionally include specific binding members, enzymes, inert particles, surfactants, ligands, detergents, etc.

"Coupled" means bound. For example, a moiety can be coupled to a microparticle by specific or nonspecific binding. As disclosed herein, the binding can be covalent or noncovalent, reversible or irreversible.

A "specific binding member" is one of two different molecules having an area on the surface or in a cavity which specifically binds to and is thereby defined as complementary with a particular spatial and polar organization of the other molecule. A specific binding member can be a member of an immunological pair such as antigen-antibody, can be biotin-avidin or biotin streptavidin, ligand-receptor, nucleic acid duplexes, IgG-protein A, DNA-DNA, DNA-RNA, RNA-RNA, and the like.

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof.

A "detectable label" is a compound or molecule that can be detected, or that can generate a readout, such as fluorescence, radioactivity, color, chemiluminescence or other readouts known in the art or later developed. The readouts can be based on fluorescence, such as by fluorescent labels, such as but not limited to, Cy-3, Cy-5, phycoerythrin, phycocyanin, allophycocyanin, FITC, rhodamine, or lanthanides; and by flourescent proteins such as, but not limited to, green fluorescent protein (GFP). The readout can be based on enzymatic activity, such as, but not limited to, the activity of beta-galactosidase, beta-lactamase, horseradish peroxidase, alkaline phosphatase, or luciferase. The readout can be based on radioisotopes (such as $^{33}P$, $^{3}H$, $^{14}C$, $^{35}S$, $^{125}I$, $^{32}P$ or $^{131}I$). A label optionally can be a base with modified mass, such as, for example, pyrimidines modified at the C5 position or purines modified at the N7 position. Mass modifying groups can be, for examples, halogen, ether or polyether, alkyl, ester or polyester, or of the general type XR, wherein X is a linking group and R is a mass-modifying group. One of skill in the art will recognize that there are numerous possibilities for mass-modifications useful in modifying nucleic acid molecules and oligonucleotides, including those described in Oligonucleotides and Analogues: A Practical Approach, Eckstein, ed. (1991) and in PCT/US94/00193.

A "signal producing system" may have one or more components, at least one component usually being a labeled binding member. The signal producing system includes all of the reagents required to produce or enhance a measurable signal including signal producing means capable of interacting with a label to produce a signal. The signal producing system provides a signal detectable by external means, often by measurement of a change in the wavelength of light absorption or emission. A signal producing system can include a chromophoric substrate and enzyme, where chromophoric substrates are enzymatically converted to dyes which absorb light in the ultraviolet or visible region, phosphors or fluorescers. However, a signal producing system can also provide a detectable signal that can be based on radioactivity or other detectable signals.

The signal producing system can include at least one catalyst, usually at least one enzyme, and can include at least one substrate, and may include two or more catalysts and a plurality of substrates, and may include a combination of enzymes, where the substrate of one enzyme is the product of the other enzyme. The operation of the signal producing system is to produce a product which provides a detectable signal at the predetermined site, related to the presence of label at the predetermined site.

In order to have a detectable signal, it may be desirable to provide means for amplifying the signal produced by the presence of the label at the predetermined site. Therefore, it will usually be preferable for the label to be a catalyst or luminescent compound or radioisotope, most preferably a catalyst. Preferably, catalysts are enzymes and coenzymes which can produce a multiplicity of signal generating molecules from a single label. An enzyme or coenzyme can be employed which provides the desired amplification by producing a product, which absorbs light, for example, a dye, or emits light upon irradiation, for example, a fluorescer. Alternatively, the catalytic reaction can lead to direct light emission, for example, chemiluminescence. A large number of enzymes and coenzymes for providing such products are indicated in U.S. Pat. Nos. 4,275,149 and 4,318,980, which disclosures are incorporated herein by reference. A wide variety of non-enzymatic catalysts which may be employed are found in U.S. Pat No. 4,160,645, issued Jul. 10, 1979, the appropriate portions of which are incorporated herein by reference.

The product of the enzyme reaction will usually be a dye or fluorescer. A large number of illustrative fluorescers are indicated in U.S. Pat. No. 4,275,149, which disclosure is incorporated herein by reference.

Other technical terms used herein have their ordinary meaning in the art that they are used, as exemplified by a variety of technical dictionaries.

Intorduction

The present invention recognizes that dielectrophoresis and traveling wave dielectrophoreses provide rapid, efficient and non-disruptive means for separating moieties in a sample. The present invention also recognizes that it is often difficult to use dielectrophoresis and traveling wave dielectrophoresis to separate moieties from other components of a sample if different components of a sample have similar dielectric properties.

The present invention addresses these and other related needs in the art. It is an objective of the present invention to provide compositions such as sample solutions that can enhance the dielectrophoretic separation of moieties in samples and can be used directly in dielectrophoretic separation processes. It is another objective of the present invention to provide methods for separating moieties using a sample solution of the present invention. It is another objective of the present invention to provide methods for separating moieties in a blood sample using electromagnetic forces and using a solution that selectively modifies red blood cells.

As a non-limiting introduction to the breath of the present invention, the present invention includes several general and useful aspects, including:

1) a solution that, when combined with a sample, modifies at least one dielectric property of at least one component of the sample and that is of a conductivity that allows dielectrophoretic separation of moieties of interest of a sample;

2) a method for dielectrophoretically separating moieties of a sample using a solution that selectively modifies the dielectric properties of at least one component of the sample and that is of a conductivity that allows dielectrophoretic separation of moieties of interest of a sample; and 3) a method for electromagnetically separating moieties of a sample using a solution that selectively modifies red blood cells, magnetic microparticles, and one or more sources of electromagnetic forces that are integral to a chip.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

A Solution that Modifies a Dielectric Property of at Least One Component of a Sample The present invention includes a sample solution that, when combined with a sample, modifies at least one dielectric property of at least one component of a sample, and results in a sample-sample solution mixture of a conductivity that allows for the dielectrophoretic separation of one or more moieties of the sample. Preferably, the conductivity of a sample solution when mixed with a sample is such that the resulting sample-sample solution mixture is less polarizable than a moiety of interest or a microparticle coupled to a moiety of interest to be separated under dielectrophoretic separation conditions. Thus, a moiety of interest or a microparticle coupled to a moiety of interest may be subjected to, and may be separated by, positive dielectrophoretic forces. However, this is not a requirement of the present invention. For example, a sample solution that when mixed with a sample results in a sample-sample solution mixture that is more polarizable than a moiety to be separated is also within the scope of the present invention. In aspects of the invention where a sample-sample solution mixture is more polarizable that a moiety to be separated, a moiety can be separated by negative dielectrophoresis or negative dielectrophoresis-based methods. The methods that can be used for the dielectrophoretic separation in the present invention include all dielectrophoretic separation techniques, including, but not limited to, dielectrophoretic migration, dielectrophoretic retention, dielectrophoretic/gravitational field flow fractionation, traveling-wave dielectrophoresis-based separation, 2-D dielectrophoresis.

Sample-sample solution mixtures of the present invention preferably have conductivities of between about 1 microSiemens/cm to about 1-Siemen/m, more preferably from about 5 microSiemens/cm to about 0.5 Siemens/m, and most preferably from about 10 microSiemens/cm to about 0.1 Siemens/m. Conductivities of sample solutions and of sample-sample solution mixtures can be measured with conductivity meters that are commercially available. Conductivities of solutions can be adjusted, for example, by the addition or chelation of salt in the solution.

Sample solutions of the present invention can be mixed with a sample at any appropriate ratio, for example, from a ratio of sample to sample solution of about 10:1 to about 1:10,000, preferably at a ratio of sample to sample solution from about 5:1 to about 1:1000, more preferably at a ratio of sample to sample solution from about 1:1 to about 1:250, and most preferably at a ratio from about 1:2 to about 1:50.

Preferably, mixing a sample solution of the present invention with a sample results in the modification of one or more components of the sample, such that one or more moieties of the sample can be separated from other components of the sample more efficiently than if the sample solution were not used, using dielectrophoretic separation methods. A moiety can be separated more efficiently by increasing the differences in response to an electric field between a moiety of interest and other components of a sample. Differences in response to a electric field can be differences in the direction of movement of a moiety of interest and other components of a sample in response to an electric field, or differences in the degree of movement of a moiety of interest and other components of a sample in response to an electric field of a given strength and duration. The one or more moieties that can be separated more efficiently after mixing a sample solution of the present invention with a sample can be one or more components of the sample that were modified by the solution, or can be components other that those modified by the solution. For example, in the first case a sample component that is not responsive to a given electric field pattern can be modified such that it exhibits positive dielectrophoresis in response to that electric field pattern. Alternatively, a sample component can be modified by the methods of the present invention can be modified such that it no longer exhibits positive dielectrophoresis in response to an electric field that is used to separate other components of the sample by dielectrophoretic retention.

Components of the sample modified by the sample solution of the present invention can be moieties that are to be retained in one or more areas of a chamber by dielectrophoretic forces, or can be components that are to be repelled from one or more areas of a chamber by dielectrophoretic forces, or can be components that are neither attracted to nor repelled from one or more areas of a chamber by dielectrophoretic forces. In these aspects, the modifying sample solution can alter a dielectric property of one or more components of a sample such that when subject to an electric field, a component that is not otherwise retained by positive dielectrophoresis in one or more areas of a chamber then can be retained by positive dielectrophoresis in one or more areas of a chamber, or can alter a dielectric property of one or more components of a sample such when subject to a given electric field, a component that does not otherwise exhibit negative dielectrophoresis can then exhibit negative dielectrophoresis, or can alter a dielectric property of one or more components of a sample such that a component subject to a given electric field that exhibits either positive or negative dielectrophoresis can be rendered insensitive to the electric field such that it no longer exhibits positive or negative dielectrophoresis.

A sample solution of the present invention that can modify more than one component of a sample can modify different components in similar ways or in different ways. For example, a sample solution of the present invention can modify two types of component such that both types of component exhibit negative dielectrophoresis under a given electric field pattern. In another example, a sample solution of the present invention can modify one component of a sample that does not otherwise exhibit positive dielectrophoresis under a given electric field pattern such that it exhibits positive dielectrophoresis in that electric field pattern, and can modify another component of a sample that does not otherwise exhibit negative dielectrophoresis under a given electric field pattern such that it exhibits negative dielectrophoresis in that electric field pattern. The modification of a dielectric property of one or more components of a sample need not be an absolute change in the response of a component to a given electric field pattern, but can also be a change, for example, in the rate of response of a component to a given electric field pattern.

Components of a sample that can be modified by a sample solution of the present invention include molecules, including biomolecules, such as nucleic acids, proteins, carbohydrates, and lipids; compounds, such as organic and inorganic compounds; complexes, such as transcription complexes or ribosomes; organelles, such as mitochondrial and nucleii; viruses; parasites, such as trypanosomes and plasmodium; and cells, including prokaryotic and eukaryotic cells. The dielectric properties of such components are their permittivity, conductivity, and size. These properties in part determine the magnitude and direction of the dielectrophoretic force acting on a particle.

For an electric field of non-uniform magnitude distribution, the dielectrophoretic force on a particle of radius r can be determined by the following equation:

$$\vec{F}_{DEP} = 2\pi \epsilon_m r^3 \chi_{DEP} \nabla E_{rms}^2 \quad (1)$$

where $E_{rms}$ is the RMS value of the field strength, the symbol $\nabla$ is the symbol for gradient-operation, $\epsilon_m$ is the dielectric permittivity of the medium, and $\chi_{DEP}$ is the particle polarization factor (or dielectrophoretic polarization factor), given by:

$$\chi_{DEP} = \text{Re}\left(\frac{\epsilon_p^* - \epsilon_m^*}{\epsilon_p^* + 2\epsilon_m^*}\right), \quad (2)$$

"Re" refers to the real part of the "complex number". The symbol $\epsilon_x^* = \epsilon_x - j\sigma_x/2\pi f$ is the complex permittivity (of the particle x=p, and the medium x=m) and $j=\sqrt{-1}$. The parameters $\epsilon_p$ and $\sigma_p$ are the effective permittivity and conductivity of the particle, respectively. When a particle exhibits a positive dielectrophoretic polarization factor ($\chi_{DEP}>0$), the particle is moved by dielectrophoretic forces toward regions where the field is the strongest. On the other hand, when a particle exhibits a negative dielectrophoretic polarization factor ($\chi_{DEP}<0$), the particle is moved by dielectrophoretic forces away from those regions where the field is strongest and toward those regions where the field is weakest.

The travelling wave dielectrophoretic force for an ideal traveling wave field acting on a particle of radius r an subjected to a traveling-wave electrical field E=E cos ($2\pi$ (ft-z/$\lambda_0$) $\vec{a}_x$ (i.e. the x-component of an E-field traveling in the $\vec{a}_x$-direction, the phase value of the field x-component being a linear function of the position along the z-direction) is given by:

$$\vec{F}_{TW-DEP} = -\frac{4\pi^2 \varepsilon_m}{\lambda_0} r^3 \zeta_{TWD} E^2 \cdot \vec{a}_z \quad (4)$$

where where E is the magnitude of the field strength, $\varepsilon_m$ is the dielectric permittivity of the medium. $\zeta_{TWD}$ is the particle traveling-wave dielectrophoretic polarization factor, given by $$\zeta_{TW-DEP} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $\varepsilon_x^* = \varepsilon_x - j\sigma_x/2\pi f$ is the complex permittivity (of the particle x=p, and the medium x=m). The parameters $\varepsilon_p$ and $\sigma_p$ are the effective permittivity and conductivity of the particle, respectively. These parameters may be frequency dependent.

The travelling wave dielectrophoretic force acts on a particle that is either oriented with or against that of the direction of propagagtion of the traveling-wave field, depending upon whether the travelling wave dielectrophoretic polarization factor is negative or positive. If a particle exhibits a positive travelling wave dielectrophoretic polarization factor ($\xi_{TW-DEP}>0$) at the frequency of operation, the travelling wave dielectrophoretic force will be exerted on the particle in a direction opposite that of the direction in which the electric field travels. On the other hand, if a particle exhibits a negative travelling wave dielectrophoretic polarization factor ($\xi_{TW-DEP}<0$) at the frequency of operation, the travelling wave dielectrophoretic force will be exerted on the particle in the same direction in which the electric field travels.

Thus, the movement of a particle in a non-uniform electric field depends in part on the size (r), permittivity ($\varepsilon_p$), and conductivity ($\sigma_p$) of the particle. The size of a particle in part determines the magnitude of the dielectrophoretic force, whereas the conductivity and permittivity of a particle influence the direction and the magnitude of a particle's movement in a non-uniform field. Accordingly, particles which have different dielectric properties but are subjected to identical electrical fields will experience different dielectrophoretic forces and different travelling wave dielectrophoretic forces.

The following discussion of the dielectric properties of particles is provided as background information for factors to be considered in the selection and derivation of compositions of the present invention. The applicants provide this model as background only, and expressly do not wish to be limited to any mechanism of action described herein.

The permittivies and conductivities of particles, such as sample components, depend upon the composition of the components. For example, a homogeneous particle such as a polystyrene bead has a single permittivity value that determines the effective permittivity of the bead, and a single conductivity value that determines the effective conductivity of the bead. These properties may be independent of the field frequency in a wide frequency range, for example, between 1 Hz and 100 MHz. Particles that have a homoegeneous bulk composition may have net surface charges. When such charged particles are suspended in a medium, electrical double layers may form at the particle/medium interfaces. Externally applied electric field may interact with the electrical double layers, causing changes in the effective conductivity and effective permittivity of the particles. The interactions between the applied field and the electrical double layers are generally frequency dependent. Thus, the effective conductivity and effective permittivity of such particles may be frequency dependent.

In contrast, non-homogeneous particles such as cells, have a membrane permittivity and an internal permittivity, and a membrane conductivity and an internal conductivity. The effective permittivity and the effective conductivity of a non-homogeneous particle is dependent on both its membarne properties and its internal properties. The effective permittivity and effective conductivity of a non-homogeneous particle are dependent on the field frequency. Different dielectric models have been developed to represent different cell types. In particlular, single-shell modeling has been applied to mammalian cells, in which cells are modeled as conducting spheres (corresponding to cell interiors) surrounded by poorly-conductihg thin shells (corresponding to cell membranes). The effective cell dielectric property is then determined by dielectric parameters of the cell interiors and membranes and can be calculated according to:

$$\varepsilon_{cell}^* = \varepsilon_{mem}^* \frac{\left(\frac{r}{r-d}\right)^3 + 2\frac{\varepsilon_{int}^* - \varepsilon_{mem}^*}{\varepsilon_{int}^* + 2\varepsilon_{mem}^*}}{\left(\frac{r}{r-d}\right)^3 - \frac{\varepsilon_{int}^* - \varepsilon_{mem}^*}{\varepsilon_{int}^* + 2\varepsilon_{mem}^*}}$$

Here is the complex permittivity $\varepsilon_x^*$ of a cell (x=cell), or its membrane (x=mem) or its interior (x=int). The parameters r and d refer to the cell radius and membrane thickness, respectively.

The frequency dependence of the dielectrophoretic polarization factor ($\chi_{DEP}$) and the travelling wave dielectrophoretic polarization factor ($\xi_{TW-DEP}$) of non-homogeneous particles such as cells arises from the frequency dependence of the particles' dielectric properties. The dielectric properties of a mammalian cell are influenced by cell size, membrane thickness, the dielectric properties of the cell membrane, and the dielectric properties of the cell interior. Typically, a viable cell has a poorly-conducting membrane (membrane conductivity is typically small, less than $10^{-4}$ Siemens/m) which encloses a moderately conducting cell interior (interior conductivity is typically high, larger than 0.1 Siemens/m). At low frequencies, the applied field the cell membrane drops across the cell membrane, and the cell membrane dominates the dielectric properties of the whole cell. Under these conditions the cell may have negative values for the dielectrophoretic polarization factor ($\chi_{DEP}<0$) and exhibit negative dielectrophoresis. As frequency is increased, the applied field gradually penetrates through the cell membrane into the cell interior, and the cell's dielectrophoretic polarization factor changes from negative to positive ($\chi_{DEP}>0$). In such a frequency range, the interaction between the cell and the applied field tends to cause the cell to exhibit positive values for the travelling wave polarization factor ($\xi_{TW-DEP}$>0). As the frequency is increased further, the cells interior properties (at first the the effective conductivity and then the effective permittivity) determine the cell's responses. The cell first exhibits positive values for the dielectrophoresis polarization factor ($\chi_{DEP}$>0) and then at even higher frequenceies exhibits gradually decreasing values for $\chi_{DEP}$. In this frequency range, the cell exhibits negative values for the travelling wave dielectrophoretic polarization factor ($\xi_{TW-DEP}$<0). The exact frequency ranges for these different regimes of dielectrophoresis and travelling wave dielectrophoresis polarization factors depend on the cell's dielectric properties and the electrical conductivity of the solution in which the cells are suspended.

Some cells, notably bacterial, fungal, and plant cells, have a cell wall in addition to a cell membrane. The dielectric properties of such complex particles are complex, with the electrical permittivities and conductivities of each of the cell wall, cell membrane, and cell interior dominating the dielectrophoretic behavior of the cells at particular field frequencies. The determination of electrical properties of the cell walls of micro-organisms and the dielectrophoretic behavior of cell wall-containing micro-organisms is described in Markx et al. (Microbiology 140: 585–591(1994)).

The overall size of a particle or a component of a sample also determines its response to an electric field, and thus is herein considered a dielectric property. A sample component's conductivity, permittivity, or size, or any combination of these properties, can be altered by a solution of the present invention.

Properties of a sample component that can be modified by a solution of the present invention to change a dielectric property of a sample component can include, but not limited to, the composition of a component (including the internal composition of a complex moiety), the net charge of a sample component, charge distribution of a sample component, surface charge of a sample component, surface charge density of a sample component, surface morphology of a sample component, dimensions of a sample component and overall size of a sample component.

A sample solution of the present invention can modify a dielectric property of one or more components of a sample of the present invention by, for example, the addition of entites to a sample component or removal of constituents of a sample component, and in so doing altering the size of the component For example, a specific binding member, such as an antibody, that recognizes a protein and that is linked to a microparticle, can be added to a sample that comprises cell lysates to allow the protein to be captured using dielectrophoretic forces. In another example, a sample comprising cells can be treated with a solution that comprises a lysing agent, such as a detergent, that can cause partial or total disintegration of all or a subset of cells such that they are no longer responsive to the dielectric field used on the sample based on the reduced size of the resulting fragments. Low osmolarity solutions that can cause lysis of certain cell types are exemplary of sample solutions of the present invention that can alter dielectric properties of one or more moieties of a sample. Such low osmolarity solutions may, preferably, have a conductivity that allows dielectrophoretic separation of one or more moieties of interest of the sample. Sample solutions that can cause an increase or decrease in the size of a sample component and thereby change a dielectric property of a sample component can include specific binding members, including specific binding members bound to other entities, such as microparticles; enzymes; detergents; surfactants; chaotropic agents; denaturing agents; salts; chelators; and the like.

A sample solution of the present invention can also modify the properties of one or more sample components of the present invention by, for example, the addition of entities to a sample component or removal of portions of a sample component and in so doing altering the net charge, charge distribution, surface charge, or surface charge density of a sample component. As used herein, entities that can be added to a component of a sample can be ions, molecules, chemical groups, polymers, particles, etc. Molecules can be any molecules, organic, inorganic, or combinations thereof, such as proteins, including antibodies, carbohydrates, lipids, steroids, detergents, etc. Portions of a sample component include subunits, including cofactors; proteins; lipids; sterols; carbohydrates; nucleic acids; organic compounds; inorganic compounds; combinations of organic and inorganic compounds; and chemical groups. Portions of a component can be removed from a component by the use of salts, chelators, denaturing agents, chaotropic agents, detergents, surfactants, enzymes, chemical reactants (such as hydrazine, piperidine, and periodate) and the like. For example, a solution of the present invention can include specific binding partners such as antibodies, including antibodies that are linked to highly charged moieties such as, for example, polylysine, that can bind to a sample component and change the net surface charge or surface charge density of a component. A solution of the present invention can also include compounds such as detergents, lipids, or polymers that can coat a sample component and alter the net surface charge or surface charge density of a sample component.

In some preferred aspects of the invention, where the components to be separated are cells or organelles, one or more cell types can be permeabilized or lysed by one or more ingredients of the solution. Where cells or organelles are permeabilized, permeabilization can be general, meaning that compounds below a certain size range can enter and exit the cell, or permeabilization can be selective, meaning that only particular compounds, such as, for example, potassium ions, can enter or exit the cell. A sample solution of the present invention that can lyse or permeabilize one or more types of cell in a sample can cause hypotonic lysis or permeabilization of one or more cells, by being of a lower osmolarity than that of one or more cell types of the present invention. Alternatively or in addition, a solution of the present invention can cause cell lysis or permeabilization by targeting cell membranes, including cell membrane proteins such as transporters and channels, and can compromise reagents such as salts, detergents, surfactants, lipids, sterols, polymers, alcohols, enzymes, ionophores, metabolic inhibitors, ion channel blockers and ion channel modifiers. Cell lysis and cell permeabilization can change the charge density, net charge, or charge distribution of a cell.

A sample solution can modify a dielectric property of a component of a sample by altering the net surface charge or surface charge density of a sample component with enzymes or chemical agents. For example, many cells have a negative net surface charge owing to negative charges of groups on carbohydrate residues of cell surface glycolipids and glycoproteins. A sample solution that includes the enzyme neuramindase can alter the net surface charge or surface charge density of a cell by enzymatically cleaving carbohydrate residues from cell surface molecules. Proteases, detergents, and even reducing agents or chelators such as EDTA can also remove proteins or other molecules from the surface of a cell and thereby modify a dielectric property of a cell.

A sample solution can also change the surface charge, surface charge density, or net charge of a sample component by causing chemical changes at the surface to the sample component. Oxidants such as periodate and reducing agents such as dithiothreitol can be present in a sample solution of the present invention and can react with and chemically alter the surfaces of sample components. Enzymes can also alter the dielectric properties of sample components by causing chemical changes at the surface of a sample component. Enzymes such as kinases, phosphatases, reductases, oxidases, etc., can be included in a sample solution of the present invention.

A sample solution can also include compounds that alter the surface composition of sample components such as cells by altering the behavior or differentiation of the cells. For example, a sample solution can contain phytohemagglutinin and interleukin-2, compounds that stimulate T lymphocytes to increase the expression of MHC and co-stimulatory molecules on their surfaces, and lead to increased complexity in cell membrane morphology, and alter cell membrane permittivity (Huang et al., Biochimica Biophys. Acta 1417: 51–62 (1999)).

Sample solutions of the present invention can also change the net charge and charge distribution of a moiety by changing the internal compositions of non-homogeneous sample components such as cells. A solution of the present invention can alter the internal composition of a nonhomogeneous sample component by introducing entities into the sample component, by removing entities from the internal portion of the component, or by causing chemical or morphological changes in the interior of the sample component. For example, cells can be loaded with charged molecules using liposomes or other carriers that are available commercially (e.g., lipofectin™, available from Life Technologies, Rockville, Md., gene porter™ available from Gene Therapy Systems, San Diego, Calif., or Influx® Pinocytic Cell-Loading Reagent available from Molecular Probes, Inc., Eugene, Oreg.) that can carry molecules and compounds into cells, including, for example, charged or uncharged polymers. A solution of the present invention can also alter the internal composition of a cell by, for example, causing the cell to export molecules or compounds. For example, a sample solution of the present invention can include one or more ionophores that can cause a cell to export ions, and thereby change the net charge and charge density of the interior of the cell. Alternatively, the activity of membrane proteins such as ion channel proteins can be altered, leading to a change in the ion composition of the interior of cells.

A sample solution can also include compounds that alter the internal composition of sample components such as cells by altering the behavior or inducing differentiation of the cells. For example, B lymphocytes can be stimulated with antigen and growth factors to increase their secretion of immunoglobulins. Their increased secretory capacity can change the internal compostion of the cells, for example, by increasing the amount of internal membrane structures. Such a change can lead to an altered internal permittivity or conductivity. Ionophores, ion channel blockers, and metabolic inhibitors and other drugs can also change the internal composition of cells, and can be included in sample solutions of the present invention.

One skilled in the art can be guided by knowlege of the components to be separated or removed from the sample in selecting and identifying compounds or reagents to be included in the sample solution. For example, a sample solution used to mix with a sample having heavily glycosylated cells known to have a high density of surface charges can include neurominadase, an enzyme that can remove carbohydrates from the surface of a cell. In another example, a specific binding member such as a divalent antibody can be included in a sample solution of the present invention, where the antibody is known to bind to the surface of mitochondria and thereby crosslink mitochondria that are to be separated using dielectrophoresis. In yet another example, monovalent antibodies specific for a certain cell type can be conjugated to highly charged groups, such as polylysine, to change the surface charge of a cell and thereby modify its dielectric properties. It is also possible to identify compounds or reagents to be used in a sample solution of the present invention by testing compounds or reagents without having a prediction of the effect of the compounds or reagents on a particular sample component. For example, metabolic inhibitors, ion channel blockers, or other drugs can differentially affect cell types in a biological sample by causing changes in their internal composition. Such changes can modify their dielectric properties.

Dielectrophoretic properties of components of samples mixed with a sample solution can be empirically tested to determine whether dielectric properties of a sample component are altered by a sample solution. For example, electrorotation measurements can allow one skilled in the art to deduce dielectric properties of sample components. Measuring the rate of rotation of a moiety in a rotating electric field and derivation of dielectric properties from such measurements are demonstrated in Huang et al., Phys. Med. Biol. 37: 1499–1517 (1992); Huang et al., Phys. Med. Biol. 40: 1789–1806 (1995); Huang et al., Biochim. Biophys. Acta 1282: 76–84 (1996); and Huang et al., Biochim Biophys. Acta 1417: 51–62 (1999). It is also possible to determine the effective conductivities of moieties, such as moieties before and after treatment with a sample solution, by measuring the change in optical absorbance of a suspension of mioeities, as discussed in Price et al., Biochim. Biophys. Acts 964: 221–230 (1988); Burt et al., and J. Phys. E Sci. Instrum. 22: 952–957 (1989). Another method for testing the dielectric properties of a moiety or sample component before and after treatment with a sample solution is to test whether they exhibit positive or negative dielectrophoresis under particular conditions on a polynomial electrode array, as described in Huang and Pethig, Meas Sci Technol 2: 1142–1146 (1991) and Markx et al., Microbiology 140: 585–591 (1994).

In addition to modifying a dielectric property of a component of a sample, a sample solution of the present invention, when mixed with a sample, preferably makes a sample-sample solution mixtures that is of a conductivity that allows for the dielectric separation of one or more moieties in the sample. In most but not all cases, one skilled in the art can have an approximate idea of a desireable conductivity range for a sample solution-sample mixture. Test sample solutions can be mixed with sample at various ratios and their conductivities can be measured with a conductivity meter. In most but not all cases, low conductivities are desirable, where a low conductivity has a conductivity less than about 0.5 Siemens/m. However, in other cases, where separations can occur by negative electrophoresis, the conductivity of the solution/sample mixture need not be lower than that of the moieties to be separated. Conductivites of sample solutions can be adjusted, for example, by the addition of salt (e.g. NaCl) or chelators (e.g. EDTA).

When relevant to the separation methodology, samples having more than one cell type can also be tested for differential lysis of one or more of the cell types, for example, in a hypotonic sample solution, by microscopic examination after mixing the hypotonic sample solution with the sample.

Certain preferred embodiments of the present invention are sample solutions having a low conductivity that, when combined with a blood sample, selectively modify red blood cells such that that they are not retained in a chamber subject to dielectrophoretic forces. In these preferred embodiments, a sample solution of the present invention preferably modifies a higher percentage of red blood cells than white blood cells, hereinafter referred to as a solution that selectively lyses red blood cells. Preferably, mixing a preferred solution of the present invention with a blood sample results in the blood sample having a ratio of intact red blood cells to intact white blood cells that is less than 20:1, more preferably less than 10:1, and most preferably less that 5:1. This can be observed microscopically. Preferred sample solutions of the present invention can be mixed with a blood sample at a ratio of from about 1:10 to about 10,000:1, preferably at a ratio from about 1:5 to about 1000:1, more preferably at a ratio from about 1:1 to about 250:1, and most preferably at a ratio from about 2:1 to about 50:1. These preferred sample solutions of the present invention have a low conductivity, meaning that their polarizability in response to an applied electric field is less than that of the moieties to be separated. Preferably, the conductivity of a sample solution of a preferred embodiment of the present invention is between about 10 mOsm and about 250 mOsm, more preferably between about 20 mOsm and about 150 mOsm, and most preferably between about 30 mOsm and about 100 mOsm.

In certain aspects of these preferred embodiments, a solution of the present invention preferably has a low osmolarity such that when added to a blood sample, the blood cells are in a hypotonic medium. In these embodiments, the final osmolarity is preferably between 20 mOsm and about 150 mOsm, most preferably between 30 mOsm and about 100 mOsm. Suitable solutes for use in low osmolarity solutions of the present invention include glycerol, sugars such as sucrose, dextrose, and mannose, and sugar alcohols such as mannitol and sorbitol. Other solutes that can be used in low osmolarity solutions of the present invention include zwitterions that have no charge at or near neutral pH, for example, glycine, alanine, gamma-aminobutyric acid, cysteine, histidine (including D-, L-, 3(J) methyl- and 1 (B) methyl-histidine), carnosine, pyridine, imidazole, and collidine (see, for example, Edman, et al. Nucl. Acids Res. 25: 4907–4914 (1997)), and zwitterionic compounds and buffering agents, such as, but not limited to, N-2-Acetoamido-2-amino-ethanesulfonic acid (ACES), N,N-Bis (2-hydroxyethyl)-2-glycine (bicine), N-2-hydroxyethyl-piperazine-N'-2-ethanesulfonic acid (HEPES), 3-(N-Morpholino) -propanesulfonic acid (MOPS), piperazine-N,N'-bis-2-ethanesulfonic acid (PIPES), N-Tris(hydroxymethyl)-methyl-2-aminoethane-sulfonic acid (TES), N-Tris(hydroxymethyl)-methylglycine (Tricine), or Tris(hydroxymethyl)-aminomethane (Tris).

Electrode arrays can be used to test sample solutions of the present invention. For example, positive or negative dielectrophoresis of components of a sample mixed with a sample solution can be observed after applying an electric field. For example, a small sample of a sample-sample solution mixture can be pipetted onto a polynomial electrode array and a sinusoidal signal at certain frequencies (e.g., between about 10 Hz to about 500 MHz) and at certain magnitude (<20 V peak-to-peak) can be applied to the electrodes. Components that experience positive dielectrophoresis collect at the electrode edges, while components that experience negative dielectrophoresis collect at the central region between the electrodes (Huang and Pethig, Meas. Sci. Technol. 2:1142–1146 (1991).

Tests for separation of moieties by dielectrophoresis can use detectable labels, where at least one moiety of a sample is detectably labeled. For example, after mixing a biological sample with a sample solution of the present invention performing a dielectrophoretic separation procedure, one cell type can be labeled using antibodies that recognize that cell type and not other cell types or components of the sample. The antibodies can be bound to a detectable label, such as, for example, a flourescent molecule, such as rhodamine, fluorescein, Texas red, phycoerythrin, phycocynanin, green flourescent protein, cyan fluorescent protein, blue fluorescent protein, yellow fluorescent protein, D.s. red protein, etc. Another cell type can optionally be labeled with a different antibody and a different detectable label. In this way, the positions of the cells carrying the fluorescent labels can be visualized and the quality of dielectrophoretic separation using a buffer of the present invention can be assessed. Sample components other than cells, such as organelles, viruses, proteins, complexes, and nucleic acids, can also be detectably labeled with antibodies to test their dielectric separation.

Other tests for separation include binding assays to test for the presence of proteins, nucleic acids, or other compounds after performing separation procedures. For example, after mixing a sample with a sample solution of the present invention and performing a cell separation procedure, the separation can be assessed by the binding of an antibody specific for a protein expressed by a given cell type, or the binding of a probe nucleic acid to a nucleic acid sequence characteristic of a particular cell type (e.g., that of a species of bacteria), etc. The detection of nucleic acid sequences and proteins that are indicative of the presence of a particular cell type or cellular component can also use enzymatic detection procedures (e.g., PCR) and assays (e.g., cytochrome P450 assays).

The dielectric separation of cells can also be monitored by loading cells with detectable labels, such as dyes, as they are known in the art. For example, cells can be loaded with BCECF-AM (available from Molecular Probes, Eugene, Oreg.) a flourescein probe that can be taken up by viable cells and there position after dielectric separation can be determined (Gascoyne et al. IEEE Transcactions 33:670–678 (1997)). A chip on which separation of cells has been tested can be viewed microscopically, or separated moieties can be flushed out of the chamber and examined and quantitated by microscopic examination, flow cytometry, or assays, such as, but not limited to cell growth assays.

A sample solution of the present invention can comprise compounds in addition to those that contribute to the selective modification of a dielectric property of one or more moieties in a sample. Such compounds can be, without limitation, salts, buffering agents, enzymes, stabilizers, preservatives, chelators (such as EDTA and EGTA), chaotropic agents, denaturing agents, detergents, anticoagulants, specific binding members, and detectable labels.

Components of the composition can optionally be provided in single or multiple containers. Compositions can be in the form of kits for carrying out the subject invention, where such kits at least include one or more solutions that selectively modifies a dielectric property of one or more components of a sample and one or more preparations comprising additional reagents such as microparticles, specific binding members, buffers, solutions and reagents, and instructional material for carrying out the subject methodology, where the instructional material could be present on a package insert, on one or more containers in kit and/or on packaging associated with the kit.

II A Method for Separating Moieties from a Sample on a Chip Using a Sample Solution that Selectively Modifies a Dielectric Property of One or More Moieties in a Sample The present invention also includes a method for separating moieties of interest of a sample on a chip, using a sample solution of the present invention that, when combined with a sample, modifies at least one dielectric property of at least one component of a sample, and results in a sample-sample solution mixture of a conductivity that allows for the dielectrophoretic separation of one or more moieties of the sample. The method includes: adding a sample solution of the present invention to a sample and separating one or more moieties of a sample using dielectrophoretic forces. The method can optionally include coupling one or more moieties to binding partners that can be manipulated by dielectrophoretic forces.

Sample Solution

A sample solution of the present invention can be any sample solution that when mixed with a sample, modifies a dielectric property of at least one component of the sample and that has a conductivity that allows for the separation of at least one moiety of the sample. Preferred solutions of the present invention are solutions that selectively lyse red blood cells, such as low osmolarity polyethylene glycol solutions, sugar solutions, or sugar alcohol solutions that when mixed with a blood sample result in a sample-sample solution mixture of an osmolarity from about 20mOsm to about 150 mOsm.

Sample

A sample can be any fluid sample, such as an environmental sample, including air samples, water samples, food samples, and biological samples, including extracts of biological samples. Biological samples can be blood, serum, saliva, urine, semen, occular fluid, extracts of nasal swabs, throat swabs, or genital swabs or extracts of fecal material. Biological samples can also be samples of organs, tissues, or cell cultures, including both primary cultures and cell lines. A preferred sample is a blood sample.

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed, processed, or partially processed, for example, a blood sample that has been centrifuged to remove serum, dialyzed, subjected to flow cytometry, had reagents added to it, etc. The processed blood sample may include, not limited to, buffy coat and cell samples separated by other methods such as flow cytometry, centrifugation density gradient, magnetic activated cell sorting. A blood sample can be of any volume. For example, a blood sample can be less than five microliters, or more than 5 liters, depending on the application.

Binding Partners

Binding partners that both bind to the moieties with desired affinity or specificity and are manipulatable with dielectrophoretic forces can optionally be used in the present methods. The use of binding partners for manipulating moieties in microfluidic systems is disclosed in U.S. patent application Ser. No. 09/636,104 filed Aug. 10, 2000, entitled "Methods for Manipulating Moieties in Microfluidic Systems", herein incorporated by reference in its entirety. The binding partners can be cells such as animal, plant, fungus or bacterium cells; cellular organelles such as nucleus, mitochondrial, chloroplasts, ribosomes, ERs, Golgi apparatuses, lysosomes, proteasomes, secretory vesicles, vacuoles or microsomes; viruses, microparticles or an aggregate or complex thereof. Preferred binding partners are microparticles.

Preferably, the microparticles used in the methods have a dimension from about 0.01 micron to about several hundred microns. Non-limiting examples of the microparticles used in the methods include plastic particles, carbon particles, polystyrene microbeads, glass beads, hollow glass spheres, metal particles, particles of complex compositions, microfabricated free-standing microstructures (e.g., Design of asynchronous dielectric micromotors by Hagedorn et al., in Journal of Electrostatics, 1994, Volume: 33, Pages 159–185). Particles of complex compositions refer to the particles that comprise or consists of multiple compositional elements, for example, a metallic sphere covered with a thin layer of non-conducting polymer film.

In choosing binding partners, the type, material, composition, structure, and size of the binding partners have to be compatible with the manipulation format in the specific applications. For example, microparticles should have appropriate dielectric properties such that they can be manipulated by the dielectrophoretic forces used in the methods.

The choice of microparticles is also related to the specific manipulation details. For example, for separation of a moiety of interest from a mixture of sample components by dielectrophoretic manipulation, the binding partner's dielectric properties should be signicficantly different from those of other sample components so that when the microparticles are coupled to the moiety of interest, the moiety of interest-binding partner complexes can be selectively manipulated using dielectrophoresis.

The moiety to be manipulated can be coupled to the surface of the binding partner with any methods known in the art. For example, the moiety can be coupled to the surface of the binding partner directly or via a linker, preferably, a cleavable linker. The moiety can also be coupled to the surface of the binding partner via a covalent or a non-covalent linkage. Additionally, the moiety can be coupled to the surface of the binding partner via a specific or a non-specific binding. Preferably, the linkage between the moiety and the surface of the binding partner is a cleavable linkage, e.g., a linkage that is cleavable by a chemical, physical or an enzymatic treatment.

Linkers can be any moiety suitable to associate the moiety and the binding partner. Such linkers and linkages include, but are not limited to, amino acid or peptidic linkages, disulfide bonds, thioether bonds, hindered disulfide bonds, and covalent bonds between free reactive groups, such as amine and thiol groups. Other linkers include acid cleavable linkers, such as bismaleimideothoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (Batra et al., *Molecular Immunol.*, 30:379–386 ((1993)). In some embodiments, several linkers may be included in order to take advantage of desired properties of each linker. Other linkers, include trityl linkers, particularly, derivatized trityl groups to generate a genus of conjugates that provide for release of the moiety at various degrees of acidity or alkalinity (U.S. Pat. No. 5,612,474). Additional linking moieties are described, for example, in Huston et al., *Proc. Natl. Acad. Sci. U.S.A.*, 85:5879–5883 (1988), Whitlow, et al., *Protein Engineering*, 6:989–995 (1993), Newton et al., *Biochemistry*, 35:545–553 (1996), Cumber et al., *Bioconj.*

*Chem.*, 3:397–401 (1992), Ladurner et al., *J. Mol. Biol.*, 273:330–337 (1997) and in U.S. Pat. No. 4,894,443. In some cases, several linkers may be included in order to take advantage of desired properties of each linker. The preferred linkages used in the present methods are those effected through biotin-streptavidin interaction, antigen-antibody interaction, ligand-receptor interaction, or nucleic complementary sequence hybridization. Linkers for binding a moiety to a micorparticle and methods of coupling linkers to microparticles are further described in U.S. patent application Ser. No. 09/636,104 filed Aug. 10, 2000, entitled "Methods for Manipulating Moieties in Microfluidic Systems", herein incorporated by reference.

In some cases, after manipulating and separating the moiety-binding partner, e.g., moiety-microparticle, the binding partners do not interfere with reactions the moieites are to be subsequently involved in. Thus, it may not be necessary to decouple the moieties from the binding partners. However, in other cases, it may be desirable or necessary to decouple the moieties from the binding partners after the manipulating step. The nature of the decoupling step depends on the nature of the moiety, the binding partner, the surface modification of the partner and the manipulation step. In some cases, the condition of the decoupling step is the opposite of the conditions that favor the binding between the moiety and the binding partner. For example, if a moiety binds to the binding partner at a high salt concentration, the moiety can be decoupled from the binding partner at a low salt concentration. Similarly, if a moiety binds to the binding partner through a specific linkage or a linker, the moiety can be decoupled from the binding partner by subjecting the linkage to a condition or agent that specifically cleaves the linker.

Chamber Comprising a Chip

A chamber of the present invention is a structure that can contain a fluid sample. A chamber can be of any size or dimensions, and preferably can contain a fluid sample of between 0.001 microliter and 50 milliliters, more preferably between about 1 microliters and about 20 milliliters, and most preferably between about 10 microliters and about 10 milliliters. Preferably, a chamber comprises a chip. A chamber can comprise any suitable material, for example, silicon, glass, metal, ceramics, polymers, plastics, etc. and can be of a rigid or flexible material. Preferred materials for a chamber include materials that do not interfere with dielectrophoresis of moieties in a sample, for example, materials that do not bind charged or polarized molecules, such as silicon, certain plastics and polymers, for example, acrylic, or glass.

Chambers used in the methods of the present invention can comprise chips, where chips are solid supports on which one or more separations, assays, or capturing procedures can be performed. A chip can comprise one or more metals, ceramics, polymers, copolymers, plastics, rubber, silicon, gels, or glass. A chip can comprise one or more flexible materials, and can comprise one or more semi-solid layers. A chip can comprise porous or non-porous materials. The micro structures or micro-scale structures such as, channels and wells and electrode. elements and electromagnetic units are incorporated into or fabricated on the substrate for facilitating physical, biophysical, biological, biochemical, chemical reactions or processes on the chip. A chip can have a small thickness in one dimension and can have large sizes in the other two dimensions. The size of the major surfaces of a chip can vary considerably and have an aera from about 1 $mm^2$ to about 0.25 $m^2$. Preferably, the size of the major surface of the chips useable in the present methods is from about 4 $mm^2$ to about 25 $cm^2$. The shape of the chips useable in the present methods can be regular shapes such as square, rectangular, circular, or oval, or can be irregularly shaped. Chip surfaces may be flat or may not be flat. Chips useable in the methods of the present invention can have one or more wells or one or more channels that can be etched or bored into a chip or built onto the surface of a chip.

For chambers with large volumes (up to 50 mL), chips of special geometries and configurations may have be used. The chips may be fabricated on flexible materials so that the chips can be folded to form tube like chambers. Multiple chips may be configured into a same chamber. The electrode elements may have to have certain configurations so that effective dielectrophoretic forces may be generated in the region of the interest in the chamber.

Preferably, in embodiments where the chamber comprises electrodes, they will be incorporated onto or within the chip, but this is not a requirement of the present invention. Electrodes on a chip can be of any shape, such as rectangular, castellated, triangular, circular, and the like. Electrodes can be arranged in various patterns, for example, spiral, parallel, interdigitated, polynomial, etc. Electrode arrays can be fabricated on a chip by microfabrication or micromachining methods known in the art, for example, electroplating, sputtering, photolithography or etching. Examples of a chip comprising electrodes include, but are not limited to, the dielectrophoresis electrode array on a glass substrate (e.g., Dielectrophoretic Manipulation of Particles by Wang et al., in IEEE Transaction on Industry Applications, Vol. 33, No. 3, May/June, 1997, pages 660–669), individually addressable electrode array on a microfabricated bioelectronic chip (e.g., Preparation and Hybridization Analysis of DNA/RNA from *E. coli* on Microfabricated Bioelectronic Chips by Cheng et al., Nature Biotechnology, Vol. 16, 1998, pages 541–546), and the capillary electrophoresis chip (e.g., Combination of Sample-Preconcentration and Capillary Electrophoresis On-Chip by Lichtenberg, et al., in Micro Total Analysis Systems 2000 edited by A. van den Berg et al., pages 307–310).

A chamber that comprises a chip useable in the methods of the present invention can comprise one or more ports, or openings in the walls of a chamber. Preferably, a port is of a shape and size that allows a conduit to engage a port for the dispensing of a sample into the chamber. A conduit can be any tube that allows for the entry of a fluid sample into the chamber. Preferred conduits for use in the present invention include tubing, for example, rubber or polymeric tubing, e.g., tygon or teflon or PEEK tubing. Alternatively, a port can provide an opening in a wall of a chamber for the dispensing of sample into the chamber by, for example, pipetting or injection.

Conduits that engage one or more ports of the sample can introduce a sample by any means, including a pump (for example, a peristaltic pump or infusion pump), pressure source syringe, or gravity feed. One or more reagents, buffers, or solutions, including, but not limited to, a solution of the present invention that selectively modifies the dielectric properties of one or more moieties in a sample, can be added to the chamber before, after, or concurrently with the addition of a sample to a chamber. It is also within the scope of the invention to mix the sample with a reagent, buffer, or solution, before adding the sample to the chamber. Such mixing can optionally occur in one or more conduits leading to a chamber, or in one or more reservoirs connected to conduits.

Addition of Sample Solution to Sample

A sample, a sample solution, and, optionally, additional solutions, buffers, preparations, or reagents, can be added to a chamber by any convenient means, such as transfer with a pipet, injection with a syringe, gravity flow through a conduit, such as tygon tubing, etc. Preferably a sample, a sample solution, and optionally other solutions, buffers, preparations, or reagents are added to a chamber in a continuous flow mode, in which a continuous stream. of fluid is injected or pumped into at least one inlet port, and non-retained sample components and fluids exit the chamber via at least one outlet port, but this is not a requirement of the present invention In a preferred embodiment of the present invention depicted in FIG. 1, a solution is added to a blood sample via a branched conduit. The rates of flow of the sample and a sample solution of the present invention are controlled by the setting of the pump such that the concentration of the solution in the final sample that enters the chamber is compatible with the separation of moieties in the sample.

A sample solution can be added to a sample before a sample is added to a chamber. A sample and sample solution can be incubated together for any length of time before adding the sample solution-sample mixture to a chamber for separation, from less than one second to several hours or even days. Sample-sample solution mixing can also occur in a conduit that leads to the chamber, as shown in FIG. 1. Alternatively, a sample can be added to a chamber and a sample solution can be added to the chamber subsequently. It is also possible to add a sample solution to a chamber before adding the sample to a chamber.

Where binding partners such as microparticles are used in the methods of the present invention, the binding partners can be provided in the sample solution, or separately. If the binding partners are added to the sample separately, they can be added before, after, or at the same time as the sample solution.

Separation Using Dielectrophoretic Forces

Separation of moieties of a sample in a chamber can occur through the application of a non-uniform electric field. Preferably, separation of moieties occurs on a chip that is part of a chamber, and application of the non-uniform electric field can be by means of controls that are external to a chamber and a chip. One or more power sources or electrical signal generators, which may be capable of varying voltage, frequency, phase, or any combination thereof, can transmit at least one electrical signal to one or more electrodes to create a spatially non-homogeneous alternating electric field. The voltage applied to the electrodes can be in the range of from about 0 to about 100 volts, more preferably from about 0 to about 15 volts, and the frequency of the electrical signal can be in the range of from about 0.01 kHz to about 500 MHz, and preferably from between about 1 kHz to about 20 MHz. These frequencies are exemplary only, as the frequency of the separation of moieties will depend upon a dielectric property of the moieties to be separated and the conductivity of the solution the moieties are suspended in.

Separation of moieties by dielectrophoretic forces can occur by any dielectrophoretic mechanism, for example, by dielectrophoretic retention, dielectrophoretic migration, dielectrophoretic/gravitational field flow fractionation, or traveling wave dielectrophoresis-based separation, or 2-D dielectrophoresis. The following examples of separations are given by way of illustration, and not by way of limitation. Dielectrophoretic retention can be employed, in which the moiety of interest is selectively retained in one or more areas of the chamber and other components of the sample are optionally washed out of the chamber by fluid flow. In a different approach of dielectrophoretic migration, one or more moieties of interest can be dielectrophoretically translocated to one or more areas of a chip and one or more other components of a sample can be dielectrophoretically repelled from those areas. It is also possible to effect a dielectric separation using dielectrophoretic/gravitational field flow fractionation, in which different moieties are levitated to different heights, or in which one or more moieties is levitated while other moieties are directed to one or more locations on the chip, and fluid flow through the chamber comprising the chip carries different sample components out of the chip at different speeds. It is also possible to direct one or more moieties of interest out of the chamber using traveling wave dielectrophoresis, to effect a separation from the other components. It is also possible to use 2-dimensional dielectrophoresis in which both dielectrophoretic forces and traveling-wave dielectrophoretic forces are exploited for separation of one or more moieties of interest from a sample (De Gasperis et al., Biomedical Microdevices 2: 41–49 (1999)).

Because a sample can comprise components whose behaviors in various dielectric field patterns is unknown, separation of moieties can be acheived and optimized by altering such parameters as electrode geometry, electric field magnitude, and electric field frequency.

The separation can be achieved by collecting and trapping the positive dielectrophoresis-exhibiting moieties on electrode edges while removing other cells with forces such as fluidic forces. Similar methods may be applied for the case of using negative dielectrophoresis-exhibiting particles for selective separation of target cells from cell mixtures where most or many cell types exhibit positive dielectrophoresis. In aspects where dielectrophoretic/gravitational field-flow fractionation, travelling wave dielectrophoresis, or 2-dimensional dielectrophoresis is used, the separation can be achieved by collecting fractions of the sample-sample solution mixture as they "elute" or flow out of, a chamber experiencing fluid flow and dielectrophoretic forces.

The descriptions of the following embodiments are provided by way of illustration, and not by way of limitation.

In the embodiment depicted in FIG. 1, a sample solution of the present invention that selectively lyses red blood cells is added to a blood sample through a branched conduit. The blood sample comprises white blood cells 120, red blood cells 100 and other blood sample components (not shown in FIG. 1). The blood sample-sample solution is directed to a chamber of the present invention that comprises a dielectrophoresis chip having an interdigitated parallel electrode array. Application of a non-uniform electric field results in the retention of white blood cells 120 at electrode surfaces. Red blood cell debris 140 and other blood sample components (not shown in FIG. 1) are flushed out of the chamber by fluid flow.

Figure 2:
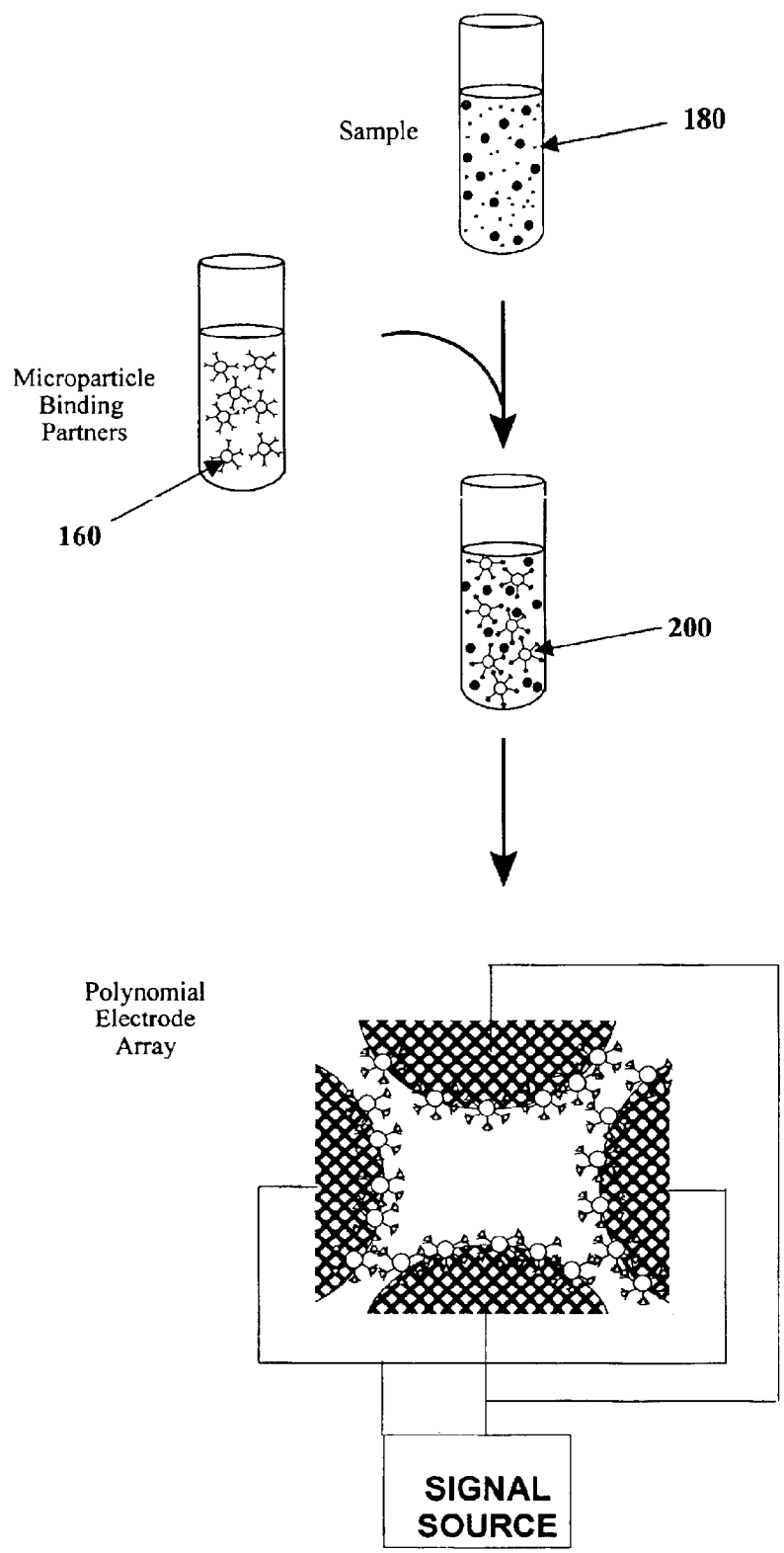
FIG. 2 depicts one aspect of a method of the present invention, in which a solution of the present invention that contains a moiety of interest (180) and a preparation of microparticles (160) is added to a sample before separating moieties bound to microparticles (200) in a sample using dielectrophoretic retention on a polynomial electrode array.

In the embodiment depicted in FIG. 2, a solution of the present invention includes specific binding partners 160 that are carbon microparticles having antibodies covalently attached to their surfaces. In this example, the antibodies bind a sample moiety 180 such as a protein of interest. The sample solution-sample mixture can be preincubated for a period of time, for example, 10 to 120 minutes, before dispensing the sample solution-sample mixture onto a chip comprising a polynomial electrode array. The incubation procedure results in the sample moiety 180 bound to binding partners 160 to form the moiety coupled to microparticle binding partners 200. Application of a nonuniform AC electric field results in retention of the protein of interest coupled to microparticles at electrode surfaces. Other sample components are washed out of the chamber, for example, by micropipet.

Figure 3:
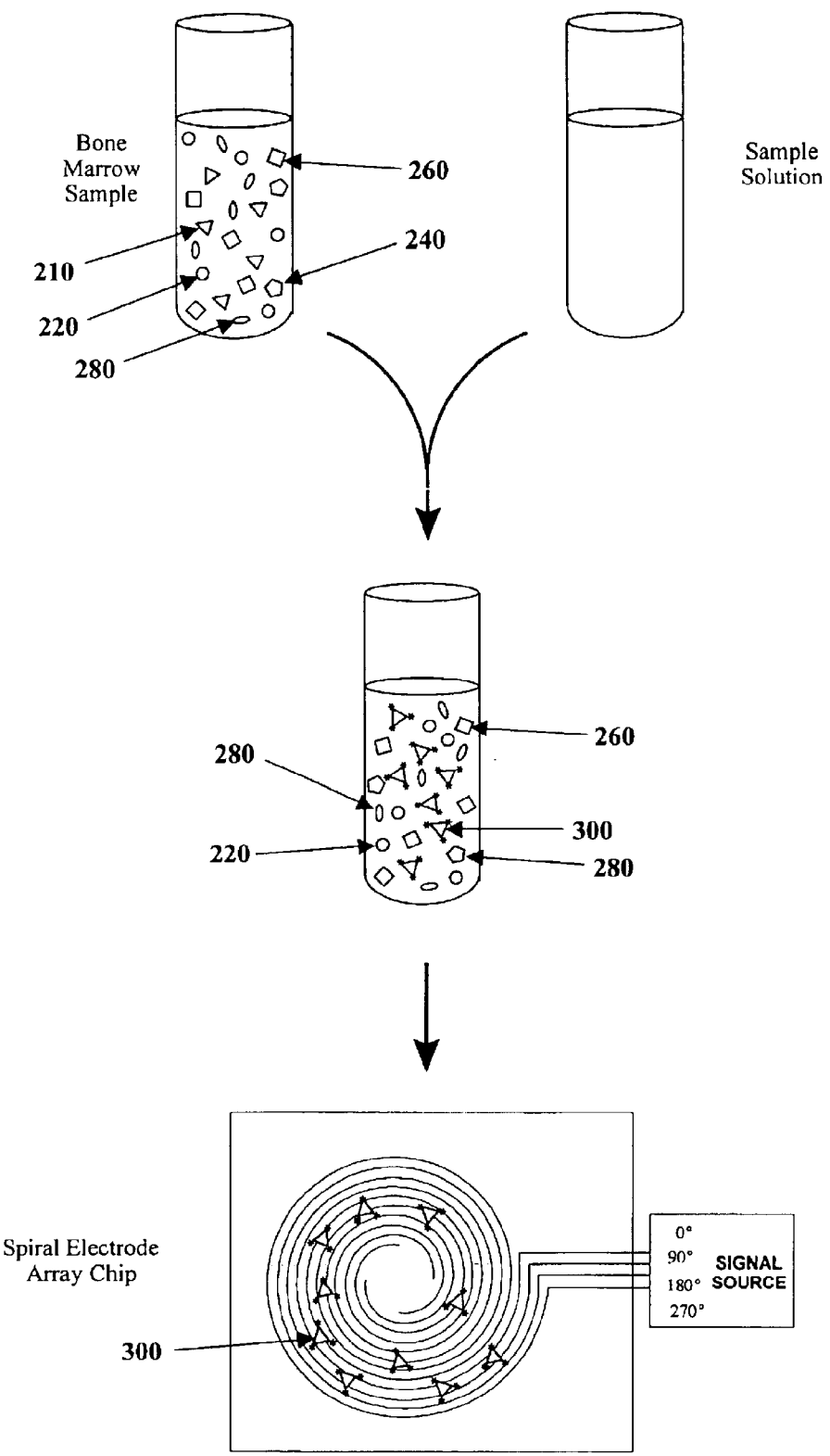
FIG. 3 depicts one aspect of a method of the present invention, in which a solution of the present invention is added to a sample to modify a moiety of the sample (210) before separating a modified moiety of interest (300) from a sample using dielectrophoretic retention on a spiral electrode array.

In the embodiment depicted in FIG. 3, a moiety of interest 210, for example stem cells isolated from bone marrow, is modified by a sample solution of the present invention that comprises antibodies that bind cell surface antigens, and that alter the surface charge of the stem cells. In addition to the moiety of interest 210, the sample comprise a number of other moieties such as progenitor and differentiated cells labeled as 220, 240, 260 and 280. The sample solution-sample mixture can be preincubated for a period of time, for example, 5 to 60 minutes, before dispensing the sample solution-sample mixture by syring injection onto a chip comprising a spiral electrode array. The altered stem cells 300 and other moieties are introduced together onto the chip. Sample buffer is pumped through the chamber, and altered stem cells 300 are isolated from progenitor and differentiated cells using dielectrophoretic retention.

Figure 4:
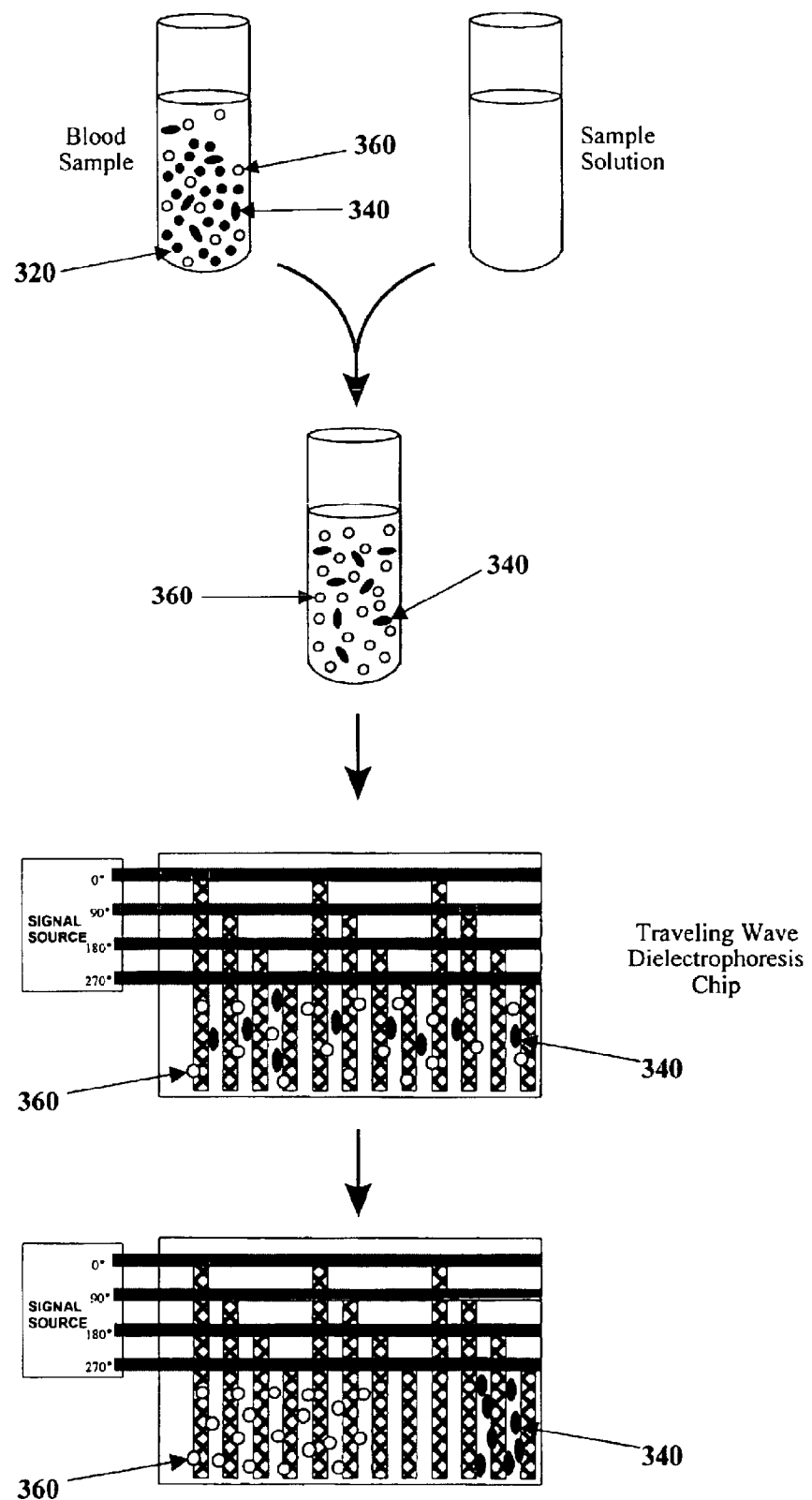
FIG. 4 depicts one aspect of a method of the present invention, in which a solution of the present invention is added to a blood sample that comprises red blood cells (320), white blood cells (360), and lymphoma cells (340), before separating lymphoma cells (340) from a sample using travelling wave dielectrophoresis.

In the embodiment depicted in FIG. 4, a solution of the present invention that selectively lyses red blood cells 320 is added to a blood sample. The blood sample comprise red blood cells 320, malignant lymphoma cells 340, non-malignant white blood cells 360, and other cells (not shown in FIG. 4). The incubation of sample solution-sample mixture cause the red blood cells being lysed with malignant lymphoma cells 340, non-malignant white blood cells 360 and other cells (not shown in FIG. 4) remained in the sample solution-sample mixture. The sample solution-sample mixture is introduced in a chamber comprising a parallel linear electrode array, and four phase-quadrature electric signals are applied to the electrodes to separate malignant lymphoma cells from nonmalignant white blood cells using traveling wave dielectrophoresis.

The above examples are given for illustrating the use of the method of dielectrophoretically separating one or more moieties in a sample using a solution of the present invention that selectively modifies at least one dielectric property of one or more components of the sample and has a conductivity such that one or more moieties of the sample can be separated using dielectrophoretic or traveling-wave dielectrophoretic forces. There are a number of dielectrophoretic methods for separating and manipulating cells, bioparticles and moieties from a sample mixture. These methods include, but not limited to, dielectrophoretic migration, dielectrophoretic retention, dielectrophoretic/gravitational field flow fractionation, traveling-wave dielectrophoresis, and 2-D dielectrophoresis. Those who are skilled in the art of dielectrophoretic manipualtion and dielectrophoretic separation may readily use and apply these methods for separating moieties of interest from a mixture in combination with the sample solution of the present invention. The following articles provide detailed descriptions of a number of dielectrophoretic manipulation and dielectrophoretic separation methods: Wang, et al., *Biochim. Biophys. Acta.* 1243:185–194 (1995), Wang, et al., *IEEE Trans. Ind. Appl.* 33:660–669 (1997) (various electrode structures, manipulation by dielectrophoresis and traveling wave dielectrophoresis); Wang, et al., *Biophys. J.* 72:1887–1899 (1997) (concentration, isolation and separation using spiral electrodes using traveling wave dielectrophoresis); Wang, et al., *Biophys. J.* 74:2689–2701 (1998), Huang, et al., *Biophys. J.* 73:1118–1129 (1997) and Yang, et al., *Anal. Chem.* 71(5):911–918 (1999) (levitation, repulsion from electrodes and separation by dielectrophoretic/gravitational field-flow-fractionation); Gascoyne, et al., *IEEE Trans. Ind. Apps.* 33(3):670–678 (1997), Becker, et al., *Proc. Natl. Acad. Sci. USA* 92:860–864 (1995) and Becker et al., *J. Phys. D: Appl. Phys.* 27:2659–2662 (1994) (trapping repulsion, redistribution and separation, separation by dielectrophoretic migration, separation by dielectrophoresis retention); Huang, et al., *J. Phys. D: Appl. Phys.* 26:1528–1535 (1993) (transportation, separation and trapping by traveling-wave-dielectrophoresis); and Wang, et al., *J. Phys. D: Appl. Phys.* 26:1278–1285 (1993) (trapping, separation and repulsion, separation by dielectrophoretic migration). All the above cited papers are incorporated in the present application by reference. Other examples of manipulation and separation methods that are reported in the literature and may be adapted for manipulating moieties using the present methods include: separation of bacteria from blood cells, and of different types of microorganisms (Hawkes, et al., *Microbios.* 73:81–86 (1993); and Cheng, et al., *Nat. Biotech.* 16:546–547 (1998)); enriching CD34+ stem cells from blood (Stephens, et al., *Bone Marrow Transplantation* 18:777–782 (1996)); DEP collection of viral particles, submicron beads, biomolecules (Washizu, et al., *IEEE Trans. Ind. Appl.* 30:835–843 (1994); Green and Morgan, *J. Phys. D: Appl. Phys.* 30:L41–L44 (1997); Hughes, et al., *Biochim. Biophys. Acta.* 1425:119–126 (1998); and Morgan, et al., *Biophys J.* 77:516–525 (1999)); dielectrophoretic levitation for cell characterization (Fuhr, et al., *Biochim. Biophys. Acta.* 1108:215–233 (1992)); single-particle homogeneous manipulation (Washizu, et al., *IEEE Trans. Ind. Appl.* 26:352–358 (1990); Fiedler, et al., *Anal. Chem.* 70:1909–1915 (1998); and Müller, et al., *Biosensors and Bioelectronics* 14:247–256 (1999)); dielectrophoretic field cages (Schnelle, et al., *Biochim. Biophys. Acta.* 1157:127–140 (1993); Fiedler, et al. (1995); Fuhr, et al. (1995a); Fiedler, et al. (1998); Müller, et al. (1999)); traveling-wave DEP manipulation of cells with linear electrode arrays (Hagedorn, et al., *Electrophoresis* 13:49–54 (1992); Fuhr, et al., *Sensors and Actuators A:* 41:230–239 (1994); and Morgan, et al., *J. Micromech. Microeng.* 7:65–70 (1997)) All the above cited papers are incorporated in the present application by reference.

III A Method for Separating Moieties of Interest from a Blood Sample on an Electromagnetic Chip Using Magnetic Microparticles and a Solution that Selectively Lyses Red Blood Cells The present invention also provides methods for separating moieties from a blood sample on an electromagnetic chip using a solution of the present invention that selectively lyses red blood cells and using microparticles that are capable of being translocated in response to electromagnetic forces. These methods include: adding a solution of the present invention that selectively lyses red blood cells to a blood sample; adding a preparation comprising one or more magnetic microparticles to the blood sample; and separating moieties of interest from the blood sample on an electromagnetic chip.

Sample Solution

A solution of the present invention that selectively lyses red blood cells can be any solution that when mixed with a blood sample, lyses a higher proportion of red blood cells than white blood cells. Preferably, mixing a solution that selectively lyses red blood cells with a blood sample results in the blood sample having a ratio of intact red blood cells to intact white blood cells that is less than 20:1, more preferably less than 10:1, and most preferably less that 5:1. This can be observed microscopically. Preferred solutions of the present invention can be mixed with a blood sample at a ratio of from about 1:10 to about 10,000:1, preferably at a ratio from about 1:5 to about 1000:1, more preferably at a ratio from about 1:1 to about 250:1, and most preferably at a ratio from about 2:1 to about 50:1.

In certain aspects of these preferred embodiments, a solution of the present invention preferably has a low osmolarity such that when added to a blood sample, the blood cells are in a hypotonic medium. In these embodiments, the final osmolarity is preferably between about 20 mOsm and about 150 mOsm, most preferably between about 30 mOsm and about 100 mOsm. Suitable solutes for use in low osmalarity solutions of the present invention include glycerol, sugars such as sucrose, dextrose, and mannose, and sugar alcohols such as mannitol and sorbitol.

Sample

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed, processed, or partially processed, for example, a blood sample that has been centrifuged to remove serum, dialyzed, subjected to flow cytometry, had reagents added to it, etc. The processed blood sample may include buffy coat and cell samples separated by other methods such as flow cytometry, centrifugation density gradient, magnetic activated cell sorting. A blood sample can be of any volume. For example, a blood sample can be less than five microliters, or more than 5 liters, depending on the application.

Magnetic Particles

Magnetic particles that are capable of being translocated in response to magnetic field and to electromagnetic forces can comprise any magnetic material (such as $\gamma Fe_2O_3$ and $Fe_3O_4$, $\gamma Fe_2O_3$ is the $\gamma$-phase of $Fe_2O_3$). Paramagnetic particles are preferred whose dipoles are induced by externally applied magnetic fields and return to zero when the external field is turned off. Suitable paramagnetic materials include, for example, iron compounds. Magnetic materials can be combined with other materials, such as polymers, in or on magnetic particles. Surfaces of magnetic particles of the present embodiment can optionally be coated with one or more compounds to facilitate attachment of specific binding members or to promote direct or indirect binding of moieties of interest. Magnetic particles of the present invention can be of any shape. Preferably magnetic particles are spherical or ellipsoid, but this is not a requirement of the present invention. The use of magnetic particles is well known in the biological and biochemical separation arts, and magnetic particles, including magnetic particles coupled to a variety of specific binding members are also commercially available (Dynal Biotech, Lake Success, N.Y.).

More than one preparation of magnetic particles can be used in the methods of the present invention. In embodiments using more than one preparation of magnetic particles, different magnetic particles can have different surface properties, such that they can bind different moieties in a sample. In this way, more that one type of moiety can be separated using the methods of the present invention. Different surface properties of magnetic particles can be conferred, for example, by coating the magnetic particles with different compounds, or by reversibly or irreversibly linking different specific binding members to the surfaces of the magnetic particles.

The moiety to be manipulated can be coupled to the surface of the binding partner with any methods known in the art. For example, the moiety can be coupled to the surface of the binding partner directly or via a linker, preferably, a cleavable linker. The moiety can also be coupled to the surface of the binding partner via a covalent or a non-covalent linkage. Additionally, the moiety can be coupled to the surface of the binding partner via a specific or a non-specific binding. Preferably, the linkage between the moiety and the surface of the binding partner is a cleavable linkage, e.g., a linkage that is cleavable by a chemical, physical or an enzymatic treatment.

Linkers can be any moiety suitable to associate the moiety and the binding partner. Such linkers and linkages include, but are not limited to, amino acid or peptidic linkages, disulfide bonds, thioether bonds, hindered disulfide bonus, and covalent bonds between free reactive groups, such as amine and thiol groups. Other linkers include acid cleavable linkers, such as bismaleimideothoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (Batra et al., *Molecular Immunol.*, 30:379–386 ((1993)). In some embodiments, several linkers may be included in order to take advantage of desired properties of each linker. Other linkers, include trityl linkers, particularly, derivatized trityl groups to generate a genus of conjugates that provide for release of the moiety at various degrees of acidity or alkalinity (U.S. Pat. No. 5,612,474). Additional linking moieties are described, for example, in Huston et al., *Proc. Natl. Acad, Sci. U.S.A.*, 85:5879–5883 (1988), Whitlow, et al., *Protein Engineering*, 6:989–995 (1993), Newton et al., *Biochemistry*, 35:545–553 (1996), Cumber et al., *Bioconj. Chem.*, 3:397–401 (1992), Ladurner et al., *J. Mol. Biol.*, 273:330–337 (1997) and in U.S. Pat. No. 4,894,443. In some cases, several linkers may be included in order to take advantage of desired properties of each linker. The preferred linkages used in the present methods are those effected through biotin-streptavidin interaction, antigen-antibody interaction, ligand-receptor interaction, or nucleic complementary sequence hybridization. Linkers for binding a moiety to a micorparticle and methods of coupling linkers to microparticles are further described in U.S. patent application Ser. No. 09/636,104, entitled "Methods for Manipulating Moieties in Microfluidic Systems", naming Xiaobo Wang, Lei Wu, Jing Cheng, Weiping Yang, and Junquan Yu as inventors and on filed Aug. 10, 2000 and corresponding PCT Application No. PCT/US00/25381, entitled "Method for Manipulating Moieties in Microfluidic Systems", filed Sep. 15, 2000, and naming Xiaobo Wang, Lei Wu, Jing Cheng, Weiping Yang, and Junquan Yu as inventors, and herein incorporated by reference in its entirety.

In some cases, after manipulating and separating the moiety-binding partner, e.g., moiety-magnetic microparticle, the binding partners do not interfere with reactions the moieites are to be subsequently involved in. Thus, it may not be necessary to decouple the moieties from the magnetic particles. However, in other cases, it may be desirable or necessary to decouple the moieties from the magnetic particles after the manipulating step. The nature of the decoupling step depends on the nature of the moiety, the particular magnetic particle, the surface modification of the magnetic particle, in particular the specific binding partner, linker, or coupling agent that may be on the magnetic particle, and the manipulation step. In some cases, the condition of the decoupling step is the opposite of the conditions that favor the binding between the moiety and the magnetic particle. For example, if a moiety binds to the magnetic particle at a high salt concentration, the moiety can be decoupled from the magnetic particle at a low salt concentration. Similarly, if a moiety binds to the magnetic particle through a specific linkage or a linker, the moiety can be decoupled from the magnetic particle by subjecting the linkage to a condition or agent that specifically cleaves the linker.

Paramagnetic particles are preferred whose magnetic dipoles are induced by externally applied magnetic fields and return to zero when external field is turned off. For such applications, commercially available paramagnetic or other magnetic particles may be used. Many of these particles are between below micron (e.g., 50 nm–0.5 micron) and tens of microns. They may have different structures and compositions. One type of magnetic particles has ferromagnetic materials encapsulated in thin latex, e.g., polystyrene, shells. Another type of magnetic particles has ferromagnetic nanoparticles diffused in and mixed with latex e.g., polystyrene, surroundings. The surfaces of both these particle types are polystyrene in nature and may be modified to link to various types of molecules.

Specific Binding Members

A preparation that includes magnetic microparticles can also include one or more specific binding members. Such binding members can comprise one or more proteins such as antibodies, antibody fragments, antigens, ligands (such as, but not limited to receptor ligands), lectins, etc. Binding members can also be organic or inorganic molecules, such as, for example, nickel, glutathione, biotin, avidin, streptavidin, non-protein receptor ligands or ligand analogues, and the like. Binding members can also comprise nucleic acids, whether RNA, DNA, or non-naturally occurring nucleic acids. One or more specific binding members can be reversibly or irreversibly bound to magnetic microparticles. Methods of conjugating molecules, such as nucleic acids and proteins, to solid surfaces are know in the art.

Electromagnetic Chip

Separations with electromagnetic particles are performed on electromagnetic chips, where the source of the electromagnetic force is in part separate from the chip and in part integral to the chip. An electrical current source is external to an electromagnetic chip of the present invention, allowing the operator to control the electromagnetic force, whereas the electromagnetic elements are fabricated onto the chip. The electromagentic elements can produce magnetic fields and exert electromagnetic forces on magnetic particles. The electromagnetic elements can be of various structural geometries. For example, the electromagentic elements can be a loop of conducting material, such as metal, that goes around a ferromagnetic body and that can be sputtered, electroplated, or deposited on a chip. An electromagnetic chip can have one or more electromagnetic units as described in the U. S. patent application Ser. No. 09/399, 299, filed Sep. 16, 1999 and U.S. patent application Ser. No. 09/685,410, filed Oct. 10, 2000, entitled "Individually Addressable Micro-Electromagnetic Unit Array Chips in Horizontal Configurations" and naming Lei Wu, Xiaobo Wang, Jing Cheng, Weiping Yang, YuXiang Zhou, LiTian Liu, and JunQuan Xu as inventors, both herein incorporated by reference.

Other examples of such electromagnetic elements include, but not limited to, those described in the following articles such as Ahn, C., et al., *J. Microelectromechanical Systems.* Volume 5: 151–158 (1996); Ahn, C., et al., *IEEE Trans. Magnetics.* Volume 30: 73–79 (1994); Liakopoulos et al., in *Transducers* 97, pages 485–488, presented in 1997 International Conference on Solid-State Sensors and Actuators, Chicago, Jun. 16–19, 1997; U.S. Pat. No. 5,883, 760 by Naoshi et al. The above publications are incorporated in the present application by reference. These publications, and the co-pending U.S. patent application Ser. No. 09/399, 299, filed Sep. 16, 1999, and the and the U.S. Pat. No. 6,716,642, filed Oct. 10, 2000, entitled "Individually Addressable Micro-Electromagnetic Unit Array Chips in Hotizontal Configurations" and naming Lei Wu, Xiaobo Wang, Jing Cheng, Weiping Yang, YuXiang Zhou, LiTian Liu, and JunXuan Xu, as inventors, both herein incorporated by reference, further disclose the materials, methods and protocols that may be used to fabricate the electromagnetic structures on a chip.

The electromagnetic chip can be fabricated on a number of materials such as ceramics, polymers, copolymers, plastics, rubber, silicon, or glass. An electromagnetic chip can be from about 1 $mm^2$ to about 0.25 $m^2$. Preferably, the size of the chips useable in the present methods is from about 4 $mm^2$ to about 25 $cm^2$. The shape of the chips useable in the present methods can be regular shapes such as square, rectangular, circular, or oval, or can be irregularly shaped. Chips useable in the methods of the present invention can have one or more wells or one or more channels that can be etched or bored into a chip or built onto the surface of a chip.

An electromagnetic chip can be a part of a chamber, where a chamber is structure capable of containing a fluid sample. A chamber can comprise any fluid-impermeable material, for example, silicon, glass, metal, ceramics, polymers, plastics, acrylic, glass, etc. Preferred materials for a chamber include materials that do not interfere with electromagnetic manipulation of moieties in a sample.

A chamber that comprises an electromagnetic chip useable in the methods of the present invention can comprise one or more ports, or openings in the walls of a chamber. Preferably, a port is of a shape and size that allows a conduit to engage a port for the dispensing of a sample into the chamber. A conduit can be any tube that allows for the entry of a fluid sample into the chamber. Preferred conduits for use in the present invention include tubing, for example, rubber or polymeric tubing, e.g., tygon or teflon or PEEK tubing. Alternatively, a port can provide an opening in a wall of a chamber for the dispensing of sample into the chamber by, for example, pipetting or injection.

Conduits that engage one or more ports of the sample can introduce a sample by means of a pump (for example, a peristaltic pump or infusion pump), pressure source syringe, or gravity feed. One or more reagents, buffers, or solutions, including, but not limited to, a solution of the present invention that selectively lyses red blood cells, or a preparation of magnetic particles, can be added to the chamber before, after, or concurrently with the addition of a sample to a chamber. It is also within the scope of the invention to mix the sample with a reagent, buffer, or solution, before adding the sample to the chamber. Such mixing can optionally occur in one or more conduits leading to a chamber, or in one or more reservoirs connected to conduits.

The chamber comprising electromagentic chip can be of any size or dimensions, and preferably can contain a fluid sample of between 0.001 microliter and 50 milliliters, more preferably between about 1 microliters and about 20 milliliters, and most preferably between about 10 microliters and about 10 milliliters. A chamber can comprise any suitable material, for example, silicon, glass, metal, ceramics, polymers, plastics, etc. and can be of a rigid or flexible material.

It is necessary to point out that for chambers with large volumes (up to 50 mL), chips of special geometries and configurations may have be used. The chips may be fabricated on flexible materials so that the chips can be folded to form tube like chambers. Multiple chips may be configured into a same chamber. The electromagnetic elements may have to have certain configurations so that effective electromagnetic forces may be generated in the region of the interest in the chamber.

Addition of Sample Solution to Sample

A sample, a sample solution, and, optionally, solutions, buffers, preparations, or reagents, including a preparation of magnetic particles can be added to a chamber by any convenient means, such as transfer with a pipet, injection with a syringe, gravity flow through a conduit, such as tygon tubing, etc. Preferably a sample, a sample solution, and optionally other solutions, buffers, preparations, or reagents are added to a chamber in a continuous flow mode, in which a continuous stream of fluid is injected or pumped into at least one inlet port, and non-retained sample components and fluids exit the chamber via at least one outlet port.

A sample solution can be added to a sample before a sample is added to a chamber. The sample and sample solution can be incubated together for any length of time before adding the sample solution-sample mixture to a chamber for separation, from less than one second to several hours to even days. Sample-sample solution mixing can occur in a conduit that leads to the chamber, as shown in FIG. 1. Alternatively, a sample can be added to a chamber and a sample solution can be added to the chamber subsequently. It is also posible to add a sample solution to a chamber before adding the sample to a chamber.

Magnetic particles can be provided in the solution that selectively lyses red blood cells, or can be added to the sample separately. If magnetic particles are added to the sample separately, they can be added before, after, or at the same time as the sample solution is added to the sample.

Addition of Sample to Electromagnetic Chip

A sample solution can be added to a sample before a sample is deposited on an electromagnetic chip or in a chamber comprising an electromagnetic chip. The sample and sample solution can be incubated together for any length of time before adding the sample solution-sample mixture to a chamber for separation, from less than one second to several hours or even days. Sample-sample solution mixing can occur in a conduit that leads to the chamber. Alternatively, a sample can be added to a chamber and a sample solution can be added to the chamber subsequently. It is also possible to add a sample solution to a chamber before adding the sample to a chamber.

Preferably, a preparation of magnetic particles is added to a sample and allowed to incubate with the sample for a period of time before the magnetic separation process. The period of time is preferably from minutes to hours and even days. The addition of a preparation of magnetic particles to a sample can occur before, after, or at the same time as the addition of a solution that selectively lyses red blood cells.

A sample, a sample solution, and, optionally, solutions, buffers, preparations, or reagents, can be added to a chamber by any convenient means, such as transfer with a pipet, injection with a syringe, gravity flow through a conduit, such as tygon, teflon, PEEK tubing, etc. Preferably a blood sample, a preparation of magnetic particles, a solution that selectively lyses red blood cells, and optionally other solutions, buffers, preparations, or reagents are added to a chamber in a continuous flow mode, in which a continuous stream of fluid is injected or pumped into at least one inlet port, and non-retained sample components and fluids exit the chamber via at least one outlet port.

One or more preparations that include microparticles can be added to the sample through one or more conduits, although this is not a requirement of the present invention. For example, one or more preparations that comprise microparticles can be added to the sample and after a period of time the sample that has incubated with the microparticles can be added to the chamber. Alternatively, the microparticles can contact the sample in one or more conduits of the chamber, and the sample is mixed with the preparation comprising microparticles as they flow into the chamber. In another aspect, one or more prepartaions that comprise microparticles can be added to the chamber via one or more conduits before, after, or concurrent with the addition of sample to the chamber. If more that one prepartion that comprises microparticles is used in a method of the present invention, the preparations can be added separately or together.

Separation Using Electromagnetic Forces

The manipulation of magnetic particles on an electromagnetic chip requires the magnetic field distribution generated over microscopic scales. One approach for generating such magnetic fields is the use of microelectromagnetic units. Such units can induce or produce magnetic field when an electrical current is applied. The switching on/off status and the magnitudes of the electrical current applied to these units will determine the magnetic field distribution. The structure and dimension of the microelectromagnetic units may be designed according to the requirement of the magnetic field distribution. The examples of the electromagnetic units include, but not limited to, those described in the following articles such as Ahn, C., et al., *J. Microelectromechanical Systems*. Volume 5: 151–158 (1996); Ahn, C., et al., *IEEE Trans. Magnetics*. Volume 30: 73–79 (1994); Liakopoulos et al., in *Transducers* 97, pages 485–488, presented in 1997 International Conference on Solid-State Sensors and Actuators, Chicago, Jun. 16–19, 1997; U.S. Pat. No. 5,883,760 by Naoshi et al. Other examples of the electromagnetic units are provided in the co-pending U.S. patent application Ser. No. 09/399,299, filed Sep. 16, 1999, and the U.S. Pat. No. 6,716,042, filed Oct. 10, 2000, entitled "Individually Addressable Micro-Electromagnetic Unit Array Chips in Horizontal Configurations" and naming Lei Wu, Xiaobo Wang, Weiping Yang, YuXiang Zhou, LiTian Lin, and JunXuan Xu as inventors, both herein incorporated by reference.

Manipulation of magnetic particles includes the directed movement, focusing and trapping of magnetic particles. The motion of magnetic particles in a magnetic field is termed "magnetophoresis". Theories and practice of magnetophoresis for cell separation and other applications may be found in various literatures (e.g., Magnetic Microspheres in Cell Separation, by Kronick, P. L. in Methods of Cell Separation, Volume 3, edited by N. Catsimpoolas, 1980, pages 115–139; Use of magnetic techniques for the isolation of cells, by Safarik I. And Safarikova M., in J. of Chromatography, 1999, Volume 722(B), pages 33–53; A fully integrated micromachined magnetic particle separator, by Ahn C. H. et al., in J. of Microelectromechanical systems, 1996, Volume 5, pages 151–157). Use of an electromagnetic chip to separate moieties bound to magnetic particles is disclosed in U. S. patent application Ser. No. 09/399,299, filed Sep. 16, 1999 and U.S. patent application Ser. No. 09/685,410, filed Oct. 10, 2000, entitled "Individually Addressable Micro-Electromagnetic Unit Array Chips in Horizontal Configurations" and naming Lei Wu, Xiaobo Wang, Jing Chen, Weiping Yang, YuXiang Zhou, LiTian Liu, and JunXuan Xu as inventors, both herein incorporated by reference.

Figure 5:
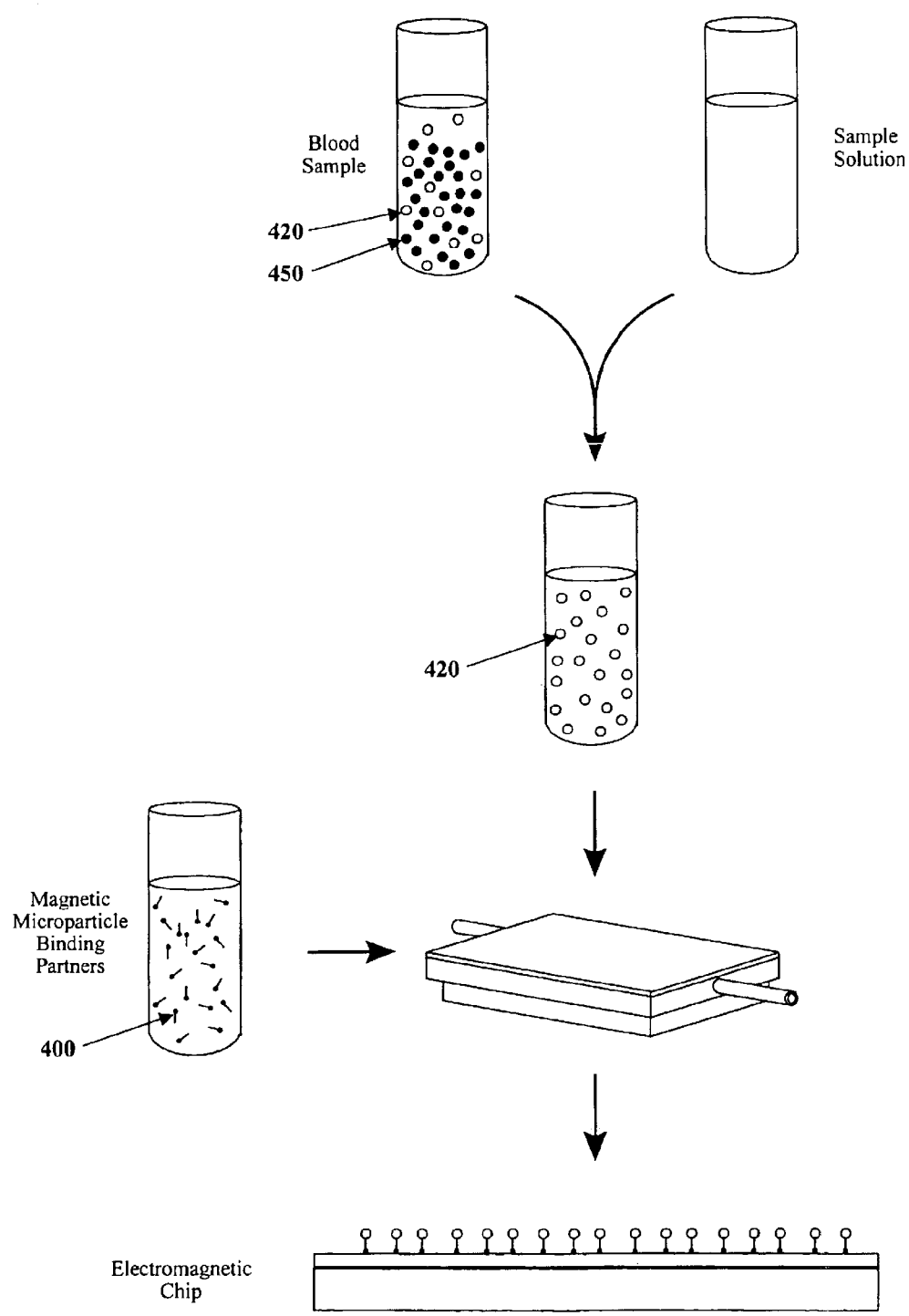
FIG. 5 depicts one aspect of a method of the present invention, in which a solution of the present invention and a preparation of magnetic microparticles (400) is added to a blood sample that comprises red blood cells (450) and white blood cells (420) before separating white blood cells bound to microparticles from the sample using electromagnetic forces.

The embodiment depicted in FIG. 5 includes a solution of the present invention that comprises magnetic microparticles 400 that comprise antibodies that specifically bind white blood cells. The blood sample comrpises white blood cells 420 and red blood cells 450 and other cells and moieties (not shown in FIG. 5). The blood sample is mixed with the sample solution of the present invention to cause red blood cells being lysed. The sample solution-sample mixture, together with a preparatioin of magnetic particles 400 is dispensed into a chamber. The sample solution-sample mixture is incubated with the magnetic particles for a specified length of the time in the chamber, resulting the magnetic particles bound to white blood cells. The chamber comprise an electromagnetic chip comprising microelectromagnetic units. Application of electric current to the micromagnetic units results in the capture of microparticles bound to white blood cells on the chip. Other sample components are washed away by pumping fluid through the chamber that comprises the electromagnetic chip.

The above examples can be varied for capturing other cell types by using antibodies against these cell types. For example, antibodies against specific surface antigens on epithelial cells can be coupled on the magentic particles. The above method can then be used to detect and capture epithelial cells such as metastatic breast cancer cells or metastatic lung cancer cells in peripheral blood taken from patients. Another example is the capture fetal cells from peripheral blood taken from pregnent mothers. In such cases, specific antibodies against fetal cells should be used for coating magnetic particles.

EXAMPLES

The following examples exemplify the characterization and use of sample solutions of the present invention that can be used to separate moieties in a sample.

Example 1

Assays of Sample Solutions that Selectively Lyse Red Blood Cells

The following solutions were tested for the selective lysis of red blood cells.

(1.1)

TABLE 1

Whole human blood is mixed with 2% (weight to weight) sucrose buffer (approximately 60 mOsm) at a ratio of 1:19. The intact white blood cells (WBC) and red blood cells (RBC) are counted under microscope at various time instants after mixing blood with the sucrose buffer. As evidenced on the Table 1, 2% sucrose solution may be used as the sample solution of the present invention.

| Detection Time (minutes) | WBC (cells/ml) | RBC (cells/ml) |
|---|---|---|
| 2 | $1.6 \times 10^5$ | $3.0 \times 10^5$ |
| 5 | $1.2 \times 10^5$ | $2.4 \times 10^5$ |
| 10 | $1.1 \times 10^5$ | $2.0 \times 10^5$ |
| 15 | $1.0 \times 10^5$ | $2.0 \times 10^5$ |
| 20 | $0.8 \times 10^5$ | $1.9 \times 10^5$ |
| 30 | $0.8 \times 10^5$ | $1.8 \times 10^5$ |

(1.2)

TABLE 2

Whole human blood is mixed with 2.2% (weight to weight) sucrose buffer (approximately 66 mOsm) at a ratio of 1:19. The intact white blood cells (WBC) and red blood cells (RBC) are counted under microscope at various time instants after mixing the blood with the sucrose buffer. As evidenced on the Table 1, 2.2% sucrose solution may be used as the sample solution of the present invention.

| Detection Time (minutes) | WBC (cells/ml) | RBC (cells/ml) |
|---|---|---|
| 2 | $2.0 \times 10^5$ | $8.1 \times 10^5$ |
| 5 | $1.9 \times 10^5$ | $8.0 \times 10^5$ |
| 10 | $1.6 \times 10^5$ | $7.8 \times 10^5$ |

TABLE 2-continued

Whole human blood is mixed with 2.2% (weight to weight) sucrose buffer (approximately 66 mOsm) at a ratio of 1:19. The intact white blood cells (WBC) and red blood cells (RBC) are counted under microscope at various time instants after mixing the blood with the sucrose buffer. As evidenced on the Table 1, 2.2% sucrose solution may be used as the sample solution of the present invention.

| Detection Time (minutes) | WBC (cells/ml) | RBC (cells/ml) |
|---|---|---|
| 15 | $1.5 \times 10^5$ | $7.7 \times 10^5$ |
| 20 | $1.2 \times 10^5$ | $6.6 \times 10^5$ |
| 30 | $0.8 \times 10^5$ | $4.9 \times 10^5$ |

(1.3)

TABLE 3

Whole human blood is mixed with various sucrose buffers at a ratio of 1:9. The cell suspension is then observed under a microscope and white (WBC) and red blood cells (RBC) are counted after 5–10 minutes. As evidenced on the Table 1, these sucrose solution may be used as the sample solution of the present invention when they are mixed with blood at certain ratios that may be different from 9:1 that is used in Table 3.

| Sucrose Concentration (weight to weight) | WBC:RBC | RBC | WBC Status |
|---|---|---|---|
| 1.3% (−39 mOsm) | 5:1–10:1 | Very few RBC left | Some WBC broken |
| 1.4% (−42 mOsm) | 1:1–1:3 | Few RBC left | Some WBC broken |
| 1.5% (−45 mOsm) | 1:5–1:10 | Some RBC left | — |
| 1.6% (−48 mOsm) | 1:10–1:20 | — | — |
| 1.8% (−54 mOsm) | 1:20–1:50 | — | Most WBC OK |
| 2.0% (−60 mOsm) | <<1:20 | Many RBC left | Most WBC OK |
| 2.2% (−66 mOsm) | <<1:20 | Many RBC left | Most WBC OK |
| 2.4% (−72 mOsm) | <<1:20 | Very many RBC left | Most WBC OK |

(1.4)

TABLE 4

Whole human blood is mixed with various sucrose buffers at a ratio of 1:24. The cell suspension is then observed under a microscope and white (WBC) and red blood cells (RBC) are counted after 5–10 minutes.

| Sucrose Concentration (weight to weight) | WBC:RBC | RBC | WBC Status |
|---|---|---|---|
| 1.3% (−39 mOsm) | — | Very few RBC left | Very few WBC left |
| 1.4% (−42 mOsm) | — | Few RBC left | Few WBC left |
| 1.5% (−45 mOsm) | — | Some RBC left | Few WBC left |
| 1.6% (−48 mOsm) | 5:1–2:1 | — | Some WBC left |
| 1.8% (−54 mOsm) | 1:1 | — | Most WBC OK |
| 2.0% (−60 mOsm) | — | Many RBC left | Most WBC OK |
| 2.2% (−66 mOsm) | <<1:20 | Many RBC left | Most WBC OK |
| 2.4% (−72 mOsm) | <<1:20 | Very many RBC left | Most WBC OK |

(1.5)

Other types of low osmolality RBC-lysis solutions, including various concentration of glycerol at 0.5%, 0.65%, 0.7%, 0.75%, 0.8% and 0.85% (weight to weight), were tested. For a dilution ratio 1:9 for blood to glycerol solution, 0.8% glycerol yielded the best result in terms of number of remaining white blood cells and white-blood-cell to red-blood-cell ratio.

(1.6)

A number of RBC lysis solutions that are currently used in the biological labs, such as a solution comprising 0.826% ammonium chloride (weight to volume), 0.1% potassium bicarbonate, and 0.0037% EDTA tetrasodium, and a solution comprising 1.1–1.2% (weight/volume) ammonium oxalate solution (210 mOsm) were also tested for comparison with solutions of the present invention. These solutions currently used in the art of blood sample processing and analysis can lyse red blood cells and cause only a small degree of lysis of white blood cells within a time window after the sample solution is added to the blood. However, the resulting sample-sample solution mixtures have very large electric conductivities and dielectrophoretic trapping or collection of white blood cells in the sample-sample solutions cannot be achieved. Furthermore, prolonged incubation (e.g., over 30 minutes) of a blood sample with these lysis solutions lead to a majority of white blood cells being lysed. These buffers are not included in sample solutions of the present invention.

Example 2

Dielectrophoretic Separation of White Blood Cells on a Chip Using Low Conductivity Solutions and Dielectrophoretic Migration and Retention Whole human blood was mixed with a sample solution of 2.0% sucrose at a ratio of 1:19. Forty microliters of the mixture was introduced by micropipet into a chamber having a volume of 40 microliters. The number of white blood cells in 40 microliters (i.e. in 2 microliter of blood) of the mixture was $10\text{-}20 \times 10^3$ cells. The chamber comprised a glass chip. The chip had an interdigitated gold/titanium electrode array, with electrodes having a characteristic dimension (i.e. electrode width, tip width, the distance between the neighbouring electrode edges) of 50 microns. An electric signal source (Hewlett Packard) was turned on to generate an electric field of 5 MHz at 5V peak-to-peak. White blood cells were collected at the electrode edges. Debris from lysed red blood cells were levitated above the electrode plane by negative dielectrophoresis and removed from the chamber by flushing the chamber with buffer using a pipet. The collected white blood cells were flushed off of the electrode surfaces and counted. The number of collected cells was $4.65 \times 10^3$.

Example 3

Dielectrophoretic Separation of White Blood Cells on a Chip Using a Solution that Selectively Lyses Red Blood Cells and Dielectrophoretic Retention Whole human blood was mixed with a sample solution of 2.0% sucrose at a ratio of 1:19. The mixture was incubated for five minutes at room temperature to allow for the lysis of red blood cells. The sample-sample solution mixture was dispensed onto a dielectrophoresis chip comprising interdigitated gold/titanium electrodes on a glass surface. The electrodes had a characteristic dimension (i.e. electrode width, tip width, the distance between the neighnbouring electrode edges) of 50 microns. A Hewlett Packard electric power source was turned on to generate an electric field of 5 MHz at 5 V peak-to-peak. White blood cells were collected at the electrode edges. The remaining sample-sample solution mixture was removed from the chamber with a pipette without touching the collected white blood cells. Collected white blood cells were harvested by flushing the electrodes with phosphate buffered saline (PBS).

The collected white blood cell samples were analyzed using PCR for the presence of the DQB genes. 1 microliter of the collected sample was added to 25 microliters of PCR reaction mix containing containing 19 microliters of $H_2O$, 2 microliter primers, 2.5 microliter PCR buffer, 0.5 microliter dNTP (10 mM), and 1 microliter Taq polymerase. The primers were obtained commercially (Sangon Corp.) and are specific for the DQB gene, and having the following sequences:

DQB1 primer 1: 5'-CATGTGCTACTTCACCAACGG-3'

DQB1 primer 2: 5'-CTGGTAGTTGTGTCTGCACAC-3'

Before adding one unit of Taq polymerase (Cetus) the reaction mixture was heated 95 degrees C. for 3 minutes, and then chilled on ice for 3 minutes. This heating-chilling cycle was repeated three times. The PCR was performed in a GeneAmp PCR System 9700, and consisted of 40 cycles of: denaturation at 94 degrees C. for 30 seconds, annealing at 55 degrees C. for 30 seconds, and extension at 72 degrees C. for 40 seconds.

The PCR products were then electrophoresed on an agarose gel. A product of the predicted size was observed, and indicated the successful isolation of white blood cells, since red blood cells are not nucleated and therefore do not contain the DQB gene.

Example 4

Magnetic Capture of White Blood Cells from a Blood Sample on an Electromagnetic Chip Using Microparticles and a Solution that Selectively Lyses Red Blood Cells A preparation of magnetic particles that bind white blood cells was prepared by adding 12.5 microliters of anti-CD15 Immunomagnetic Separation beads (Dynal) and 12.5 microliters of anti-CD45 Immunomagnetic Separation beads (Dynal) to a microfuge tube. A magnet was applied to the tube and beads were collected onto the wall for 30 seconds. The supernatant was removed. The magnet was then removed and 25 microliters of the PBS/BSA buffer (Phosphate Buffered Saline, pH 7.4, comprising 0.1% BSA and 0.6% NaCitrate) supplied by Dynal in the leukocyte magnetic isolation kit was added to the tube and the beads were resuspended. The beads were captured again with a magnet and the beads were again resuspended in an aliquot of 25 microliters of the PBS/BSA buffer. The beads were captured once more with a magnet and the buffer was removed.

One hundred microliters of a cold blood sample was added to a solution of 2% sucrose at a ratio of 1:19. The solution was incubated at room temperature for five minutes to lyse red blood cells. The washed preparation of anti-CD15 Immunomagnetic Separation beads (Dynal) and anti-CD45 Immunomagnetic Separation beads (Dynal) were added to the blood sample-sample solution. The blood sample-sample solution mixture and beads were mixed by pipetting. The beads and blood were incubated at 2–8 degrees C. for about 15 minutes. The blood sample-sample solution-magnetic particles mixture was then added to an electromagnetic chip comprising a silicon substrate having an electromagnetic unit comprising loops of electrical conductor around a ferromagnetic core that was electrically insulated from the conductive loops.

White blood cells that bound to the magnetic particles were separated by initiating an electric current through the conductive loops by means of a DC power supply manufactured by Keithley. This caused the white blood cells bound to magnetic particles to adhere to the surface of the chip. Other components of the blood sample were flushed off of the chip by fluid flow. The attachment of white blood cells could be observed microscopically.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

BIBLIOGRAPHY

U.S. Pat. No. 4,160,645
U.S. Pat. No. 4,275,149
U.S. Pat. No. 4,318,980
U.S. Pat. No. 4,326,934 issued Apr. 27, 1982 to Pohl.
U.S. Pat. No. 4,390,403 issued Jun. 28, 1983 to Batchelder
U.S. Pat. No. 4,894,443.
U.S. Pat. No. 5,344,535 issued Sep. 6, 1994 to Betts and Hawkes.
U.S. Pat. No. 5,454,472 issued Oct. 3, 1995 to Benecke et al.
U.S. Pat. No. 5,569,367 issued Oct. 29, 1996 to Bett et al.
U.S. Pat. No. 5,612,474
U.S. Pat. No. 5,653,859 issued Aug. 5, 1997 to Parton et al.
U.S. Pat. No. 5,795,457 issued Aug. 18, 1998 to Pethig, et al.
U.S. Pat. No. 5,814,200 issued Sep. 29, 1998 to Pethig et al.
U.S. Pat. No. 5,858,192 issued Jan. 12, 1999 to Becker et al.
U.S. Pat. No. 5,883,760
U.S. Pat. No. 5,888,370 issued Mar. 30, 1999 to Becker et al.
U.S. Pat. No. 5,993,630 issued Nov. 30, 1999 to Becker et al.
U.S. Pat. No. 5,993,631 issued Nov. 30, 1999 to Parton et al.
U.S. Pat. No. 5,993,632 issued Nov. 30, 1999 to Becker et al.
PCT/US94/00193.
Ahn, C., et al., IEEE Trans. Magnetics. Volume 30: 73–79 (1994).
Ahn C. H. et al., in J. of Microelectromechanical systems, Volume 5, pages 151–157, (1996).
Batra et al., Molecular Immunol., 30:379–386 (1993).
Becker, et al., J. Phys. D: Appl. Phys. 27:2659–2662 (1994).
Becker et al., Proc. Natl. Acad. Sci. USA 92: 860–864 (1995).
Burt et al., and J. Phys. E Sci. Instrum. 22: 952–957 (1989).
Cheng et al., Nat. Biotech. 16: 546–547 (1998).
Cumber et al., Bioconj. Chem., 3:397–401 (1992).
De Gasperis et al., Biomedical Microdevices 2: 41–49 (1999).
Eckstein, ed., Oligonucleotides and Analogues: A Practical Approach (1991).
Edman, et al., Nucl. Acids Res. 25: 4907–4914 (1997).
Fiedler, et al., Anal. Chem. 70:1909–1915 (1998).
Fiedler, et al. Microsystem Technologies 2: 1–7 (1995).
Fuhr, et al., Biochim. Biophys. Acta. 1108:215–233 (1992).
Fuhr, et al., Sensors and Actuators A: 41:230–239 (1994).
Fuhr, et al. Cellular Engineering Autumn: 47–57 (1995).
Fuhr et al., Sensors and Materials 7: 131–146 (1995).
Gascoyne et al. IEEE Transcactions 33:670–678 (1997).
Green and Morgan, J. Phys. D: Appl. Phys. 30: L41-L44 (1997).
Hagedorn, et al., Electrophoresis 13:49–54 (1992).
Hagedorn et al., Journal of Electrostatics, 33, 159–185 (1994).
Hawkes et al., Microbios. 73: 81–86 (1993).
Huang and Pethig, Meas Sci Technol 2: 1142–1146 (1991).
Huang et al., Phys. Med. Biol. 37: 1499–1517 (1992).
Huang et al. J. Phys. D: Appl. Phys. 26: 1528–1535 (1993).
Huang et al. Phys. Med. Biol. 40: 1789–1806 (1995).
Huang et al. Biochim. Biophys. Acta 1282: 76–84 (1996).
Huang et al., Biophys. J. 73:1118–1129 (1997).
Huang et al., Biochimica Biophys. Acta 1417: 51–62 (1999).
Hughes et al., Biochim. Biophys. Acta 1425:119–126 (1998).
Huston et al., Proc. Natl. Acad. Sci. U.S.A., 85:5879–5883 (1988).
Kronick, P. L., in Methods of Cell Separation, Volume 3, edited by N. Catsimpoolas, pages 115–139 (1980).
Ladurner et al., J. Mol. Biol., 273:330–337 (1997).
Liakopoulos et al., in Transducers 97, pages 485–488, presented in 1997 International Conference on Solid-State Sensors and Actuators, Chicago, Jun. 16–19, 1997.
Lichtenberg, et al., in Micro Total Analysis Systems 2000, edited by A. van den Berg et al., pages 307–310.
Markx et al., Microbiology 140: 585–591 (1994).
Morgan et al., Biophys. J. 77: 516–525 (1999).
Morgan, et al., J. Micromech. Microeng. 7:65–70 (1997).
Müller, et al., Biosensors and Bioelectronics 14:247–256 (1999).
Newton et al., Biochemistry, 35:545–553 (1996).
Price et al. Biochim. Biophys. Acts 964: 221–230 (1988).
Safarik I. And Safarikova M., in J. of Chromatography, Volume 722(B), pages 33–53 (1999).
Schnelle, et al., Biochim. Biophys. Acta. 1157:127–140 (1993).
Stephens et al., Bone Marrow Transplantation 18: 777–782 (1996).
Wang, et al., J. Phys. D: Appl. Phys. 26:1278–1285 (1993).
Wang et al., Biochim, Biophys. Acta 1243: 185–194 (1995).
Wang et al. IEEE Transaction on Industry Applications 33: 660–669 (1997).
Wang et al. Biophys. J. 72: 1887–1899 (1997).
Wang, et al., Biophys. J. 74:2689–2701 (1998).
Washizu, et al., IEEE Trans. Ind. Appl. 26:352–358 (1990).
Washizu, et al., IEEE Trans. Ind. App. 30: 835–843 (1994).
Whitlow, et al., Protein Engineering, 6:989–995 (1993).
Yang, et al., Anal. Chem. 71(5):911–918 (1999).

What is claimed is:

1. A method of separating one or more moieties from a blood sample, comprising:
   a) adding to said blood sample a solution that selectively lyses red blood cells, such that when said solution that selectively lyses red blood cells is added to said blood sample, said blood sample has a low conductivity and an osmolarity of from about 20 mOsm to about 150 mOsm;
   b) adding at least one preparation comprising one or more magnetic microparticles to said blood sample; wherein said one or more magnetic microparticles comprise one or more binding members specific for one or more moieties of interest;
   c) adding said blood sample to an electromagnetic chip; and
   d) subjecting said blood sample to electromagnetic forces, such that said one or more moieties of interest are selectively retained in one or more areas of said chip.

2. The method of claim 1, wherein when said solution that selectively lyses red blood cells is added to said blood sample, said blood sample has a conductivity of from about 1 microSiemen/cm to about 1 Siemen/m.

3. The method of claim 2, wherein when said solution that selectively lyses red blood cells is added to said blood sample, said blood sample has a conductivity of from about 5 microSiemens/cm to about 0.5 Siemen/m.

4. The method of claim 3, wherein when said solution that selectively lyses red blood cells is added to said blood sample, said blood sample has a conductivity of from about 10 microSiemens/cm to about 0.1 Siemen/m.

5. The method of claim 1, wherein when said solution that selectively lyses red blood cells is added to said blood sample, said blood sample has an osmolarity of from about 30 mOsm to about 100 mOsm.

6. The method of claim 5, wherein when said solution that selectively lyses red blood cells is added to said blood sample, the ratio of intact red blood cells to intact white blood cells is less than 20:1.

7. The method of claim 6, wherein when said solution that selectively lyses red blood cells is added to said blood sample, the ratio of intact red blood cells to intact white blood cells is less than 10:1.

8. The method of claim 7, wherein when said solution that selectively lyses red blood cells is added to said blood sample, the ratio of intact red blood cells to intact white blood cells is less than 5:1.

9. The method of claim 1, wherein said solution that selectively lyses red blood cells is added to said blood sample at a ratio of from about 1:10 to about 10,000:1.

10. The method of claim 9, wherein said solution that selectively lyses red blood cells is added to said blood sample at a ratio of from about 1:5 to about 1,000:1.

11. The method of claim 10, wherein said solution that selectively lyses red blood cells is added to said blood sample at a ratio of from about 1:1 to about 200:1.

12. The method of claim 11, wherein said solution that selectively lyses red blood cells is added to said blood sample at a ratio of from about 2:1 to about 50:1.

13. The method of claim 1, wherein said solution that selectively lyses red blood cells comprises glycerol, one or more sugars, one or more sugar alcohols, or one or more zwitterions or zwitterionic compounds.

14. The method of claim 13, wherein said solution that selectively lyses red blood cells comprises glycerol.

15. The method of claim 14, wherein when said solution that selectively lyses red blood cells is added to said blood sample, said blood sample comprises a concentration of glycerol of from about 0.075% to about 0.085%.

16. The method of claim 13, wherein said solution that selectively lyses red blood cells comprises sucrose, mannose, mannitol, or sorbitol.

17. The method of claim 16, wherein said solution that selectively lyses red blood cells comprises sucrose.

18. The method of claim 17, wherein when said solution that selectively lyses red blood cells is added to said blood sample, said blood sample comprises a concentration of sucrose of from about 0.05% to about 0.15%.

19. The method of claim 1, wherein said moieties of interest are cells.

20. The method of claim 19, wherein said cells are white blood cells, cancer cells, stem cells, progenitor cells, fetal cells, bacterial cells, or cells infected with an etiological agent.

21. The method of claim 1, wherein said moieties of interest are viruses.

22. The method of claim 1, wherein said chip comprises at least a part of the source of said electromagnetic forces.

23. The method of claim 1, wherein said one or more specific binding members comprises at least one antibody or antibody fragment.

24. The method of claim 1, wherein said magnetic microparticles comprise metal, ceramics, glass, plastics, or at least one polymer.

25. The method of claim 1, wherein said magnetic microparticles are from 2 microns to 50 microns in diameter.

26. The method of claim 1, wherein said adding at least one preparation comprising one or more magnetic microparticles to said blood samples occurs before adding said blood sample to said electromagnetic chip.

27. The method of claim 1, wherein said adding at least one preparation comprising one or more magnetic microparticles to said blood samples occurs after adding said blood sample to said electromagnetic chip.

* * * * *